United States Patent [19]

Hollman et al.

[11] Patent Number: 5,264,864
[45] Date of Patent: Nov. 23, 1993

[54] CHART RECORDER

[75] Inventors: William Hollman, Seattle; Fremont W. Burrows, Kent; John T. Rotunda, Renton, all of Wash.

[73] Assignee: Quinton Instrument Company, Seattle, Wash.

[21] Appl. No.: 733,998

[22] Filed: Jul. 22, 1991

[51] Int. Cl.$^5$ .................. B41J 11/42; B41J 29/44; A61B 5/0432; B65H 7/02

[52] U.S. Cl. .................. 346/1.1; 128/710; 271/265; 346/33 ME; 346/134; 346/136; 400/582; 400/583; 400/708

[58] Field of Search .......... 346/136, 134, 33 ME, 346/17, 1.1; 400/582, 583, 618, 630, 706, 708, 120 HE, 583.3; 128/710; 271/265, 272-274; 226/27-30, 45; 395/111

[56] References Cited

U.S. PATENT DOCUMENTS

| | | | |
|---|---|---|---|
| 2,805,113 | 9/1957 | Brown, Jr. et al. | 346/49 |
| 3,107,064 | 10/1963 | Price et al. | 242/55 |
| 3,364,498 | 1/1968 | Kawase et al. | 346/136 |
| 3,717,881 | 2/1973 | Bunning | 346/136 |
| 3,785,639 | 1/1974 | Ziebka et al. | 271/46 |
| 3,792,825 | 2/1974 | Kampf | 242/67.3 R |
| 3,827,544 | 8/1974 | Smith | 197/133 R |
| 3,854,145 | 12/1974 | Carroll, Jr. et al. | 346/116 |
| 3,972,460 | 8/1976 | Kesinger et al. | 226/6 |
| 4,050,079 | 9/1977 | Pegnim et al. | 346/145 |
| 4,107,700 | 8/1978 | Jornod | 346/76 R |
| 4,213,135 | 7/1980 | Medvecky | 346/76 PH |
| 4,214,590 | 7/1980 | Patnoi et al. | 128/710 |
| 4,237,466 | 12/1980 | Scranton | 346/76 |
| 4,370,665 | 1/1983 | Scranton et al.] | 346/136 X |
| 4,396,926 | 8/1983 | Manning et al. | 346/145 |
| 4,425,571 | 1/1984 | Mueller et al. | 346/136 |
| 4,511,904 | 4/1985 | Takahashi | 346/134 |
| 4,533,926 | 8/1985 | Foldvari et al. | 346/136 |
| 4,560,990 | 12/1985 | Sue et al. | 346/17 |
| 4,560,995 | 12/1985 | Suga et al. | 346/136 |
| 4,581,618 | 4/1986 | Watanabe et al. | 346/134 |
| 4,598,298 | 7/1986 | Groenke et al. | 346/1.1 |
| 4,699,374 | 10/1987 | Hain | 271/267 |
| 4,734,868 | 3/1988 | DeLacy | 364/519 |
| 4,766,446 | 8/1988 | Abe et al. | 346/136 |
| 4,786,920 | 11/1988 | Igarashi | 346/134 |
| 4,789,259 | 12/1988 | Katayanagi | 400/624 |
| 4,834,568 | 5/1990 | Kagami et al. | 400/708 X |
| 4,900,173 | 2/1990 | Okamura | 400/606 |
| 4,910,530 | 3/1990 | Fukumoto et al. | 346/134 X |
| 4,953,994 | 9/1990 | Shiozaki et al. | 400/708 X |
| 4,962,388 | 10/1990 | Quedens et al. | 346/136 |
| 4,972,207 | 11/1990 | Ishiyama et al. | 346/76 PH |
| 4,999,649 | 3/1991 | Saji et al. | 346/134 |

FOREIGN PATENT DOCUMENTS 0372753 6/1990 European Pat. Off. .
627638 1/1982 Switzerland .

*Primary Examiner*—Benjamin R. Fuller
*Assistant Examiner*—Alrick Bobb
*Attorney, Agent, or Firm*—Andrew J. Beck; Montgomery W. Smith; Curtis D. Kinghorn

[57] ABSTRACT

A chart recorder (10) is disclosed having an automatic paper loading system, an automatic tensioning system and an "odometer" system for determining the amount of paper moved through the chart recorder. The chart recorder (10) includes a print roller (34) and a feed roller (22), both in frictional contact with the paper in the recorder and both connected to and rotated by a motor. The feed roller (22) is connected to the motor through a one way clutch that allows the feed roller (22) to "free wheel" when the feed roller (22) is rotated at a faster rate, due to frictional contact with the paper, than the roller would be rotated by the motor (56). Dissipative forces in the one way clutch (68) and bearings (24) of the feed roller (22) cause it to resist being rotated which imparts tension to the paper and draws it into contact with a paper guide (14). The chart recorder (10) also has a system for positioning the paper at the top of form position before printing begins and an "odometer" system for determining the amount of paper moved through the chart recorder. The "odometer" system includes a timer for measuring the length of time the paper is moved through the chart recorder and a control system, preferably including a microprocessor, which multiplies the length of time the paper has moved through the chart recorder by the rate that the paper is moved through the chart recorder to determine the length of paper moved through the chart recorder.

39 Claims, 7 Drawing Sheets

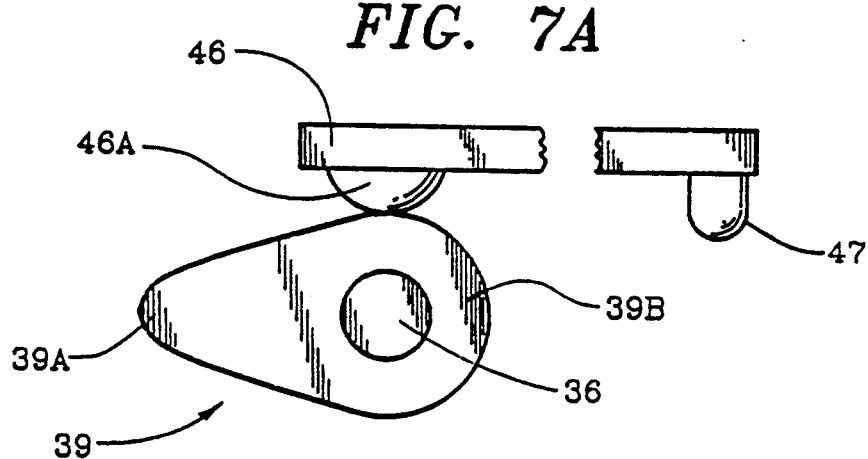
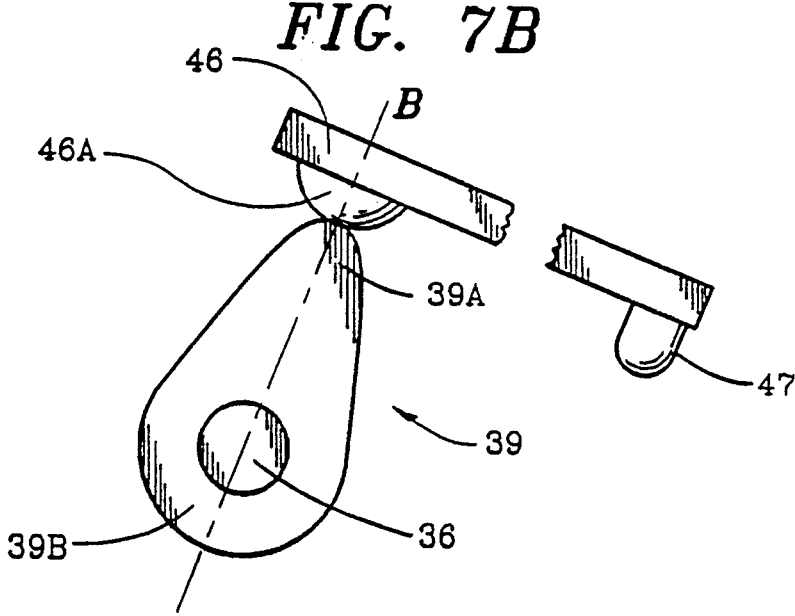
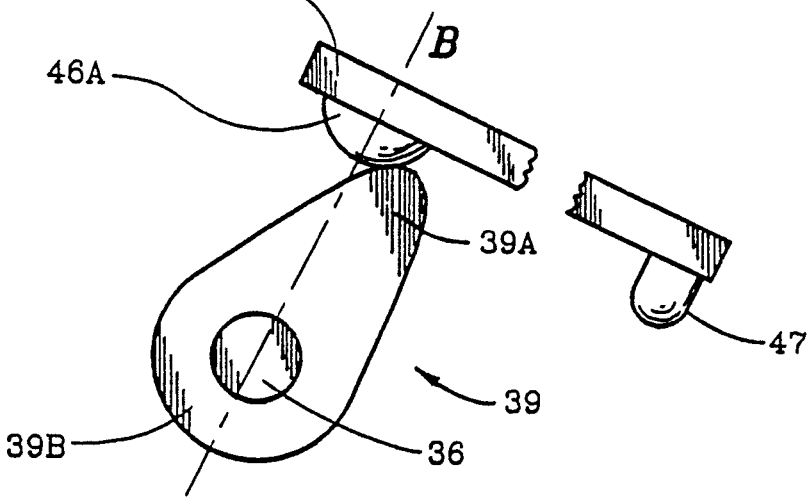

CHART RECORDER

BACKGROUND OF THE INVENTION

1. Field of the Invention

The instant invention relates to a chart recorder for printing electrical signals on paper, and more specifically to a chart recorder for printing electrocardiogram (ECG) signals on paper having precisely positioned graphic lines preprinted on the paper to form a grid pattern, which chart recorder automatically loads the paper into the recorder, has a drag inducing system to impart drag to the paper to hold it precisely in position within the recorder for precise printing and includes an odometer system for determining the amount of paper passing through the recorder.

2. Description of Related Art

Many recorders exist for recording ECG signals on paper. Typically, these recorders pass paper between a print roller and a print head so that the print head prints a representation of the ECG signal on the paper. Often the paper used in these recorders has preprinted grid lines so that reference to certain points of the printed ECG signal may be more easily made.

The Association for the Advancement of Medical Instrumentation (AAMI), the professional organization setting standards in the medical profession for recording ECG signals, has set standards regarding alignment of the preprinted grid lines on the printing paper with the printed ECG signal. The AAMI standard is that no more than one half millimeter of misalignment is allowed along the length of the printing device which is typically a thermal print head. This standard approximates the goal of having a straight vertical line printed by the printing device on the paper be exactly parallel to the vertical grid lines of the paper. This allows identical amplitudes of an ECG signal to be printed on the paper parallel to the vertical grid lines as shown in FIG. 1A.

However, often the paper becomes misaligned within the recorder. This misalignment causes the printed ECG signal to be misaligned with the preprinted grid lines as shown in FIG. 1B. This misalignment may be the result of improper loading, a lack of precision formed and fitted pieces within the recorder, or the lack of proper positioning or alignment of the paper within the chart recorder.

The lack of proper positioning of the paper within the recorder often occurs because of a lack of tension on the paper in the recorder. The lack of tension on the paper allows the paper to pull or bind within the recorder in response to movement of or uneven contact with the feeding mechanism of the recorder or as a result of uneven contact with the printing device. This problem is exacerbated by misalignment within the feeding system itself so that parts of the paper are pushed or pulled in greater or lesser amounts as compared to other parts of the paper. In addition, parts of the paper may be caught or bound within the recorder. The pushing, pulling or binding causes lateral forces on the paper as it moves through the recorder. These lateral forces move the paper sideways or cause it to twist within the chart recorder. This sideways or twisting movement causes the paper to be misaligned with the print head.

Another contributing cause of misalignment of paper within the recorder, as shown in FIG. 3, is due to the passage of folds 3 in the paper 2 through the recorder 10. The folds 3 result from using paper 2 prefolded at single page intervals to allow the paper to be conveniently stored and to lay flat after printing. As shown in FIG. 3, as the folds 3 pass through a paper guide 14 in the direction of arrow A, the lack of tension in paper 2 allows the paper near the fold 3 to bow away from and out of contact with the inner guide 16.

Inner guide 16 includes guides extending along the path of the paper 2 through the paper guide 14. The guides extend along the side edges of the paper 2 and are precisely made to be separated by the width of the paper 2 plus a nominal tolerance. The guides are preferably the side walls themselves of the paper guide 14 but may be channels recessed in the inner guide 16. The side edges of paper 2 contact the edges of the guides in inner guide 16. This contact between the edges of the guides or channels and the edges of paper 2 holds paper 2 in position on inner guide 16. When paper 2 is not in contact with inner guide 16, the guides of inner guide 16 cannot precisely position the paper 2. This leads to misalignment of the paper 2.

One solution to the misalignment problem caused by lack of tension on the paper has been to place a weight on the paper being input to the recorder. One embodiment of this type has the weight at the end of a swing arm connected to a pivot. The weight pivots on the swing arm around an attachment point under the force of gravity and contacts the paper, pinching the paper between the weight and a support surface. The weight applies tension to the paper through frictional contact with the paper as the paper is moved through the recorder.

This pivoted weight is typically located on the input side of the paper guide while a drive mechanism for moving the paper through the recorder is typically located on the opposite or output side of the paper guide. When the paper is pulled through the recorder by such a drive mechanism, the tension imparted to the paper by the pivoting weight causes the paper to come into taught contact with an inner guide surface, having guides or channels, within the paper guide prior to the paper being passed to the print head. The guides or channels of the inner guide surface then position the paper prior to being presented to the print head. While this type of tension creating device works, it is costly to manufacture, cumbersome to operate and prone to breakdown.

Another problem commonly occurring with prior art chart recorders is that they must be manually loaded with paper prior to their useful operation. Typically, this loading involves precisely positioning paper manually at an inlet to the chart recorder and thereafter manually moving the paper through the paper guide into position at the print head in order to receive printing. This process is often tedious and time-consuming which causes aggravation, frustration and annoyance to the users of such recorders which often results in inaccurate alignment of the paper. Improper alignment of the paper during the loading process is a leading cause of misalignment of the paper at the print head.

SUMMARY OF THE INVENTION

In view of the foregoing problems with the prior art, it is highly desirable to create a system for automatically loading the paper which simultaneously precisely positions the paper within the recorder for printing by a printing device.

Further, it is highly desirable to provide a system for simply and effectively imparting tension to the paper within the guide structure of the recorder to aid in precisely aligning the paper as it is presented to the printing device.

Further, it is highly desirable to provide a system for automatically detecting the "top of form" of the individual sheets of paper and thereafter for precisely positioning the paper within the recorder with respect to the "top of form".

Lastly, it is highly desirable in a chart recorder having a "top of form" sensing system to provide a system for printing ECG signals on paper which may be operated in the event of a failure of the "top of form" sensing system.

These and other desirable features of a chart recorder are incorporated in the instant invention.

A chart recorder having an automatic paper loading system which precisely positions the paper within the chart recorder for printing of electrical signals, such as ECG signals, by a print head is disclosed. The paper, when loaded into the chart recorder at a paper input, passes between a pinch or snub roller and a feed roller, through a curved paper guide having inner and outer guide surfaces, and between a print roller and the print head. The print roller and feed roller both have the same outer diameter. The print roller is connected to a rotating motor shaft by a belt extending between a pulley attached to the rotating shaft and a pulley attached to the end of the print roller. Another belt connects the print roller pulley to a pulley connected around a one-way clutch on the end of the feed roller. The clutch allows rotation of the pulley to be transferred to the feed roller when the pulley is rotated in a certain direction. When the pulley is rotated in the opposite direction, no transfer of rotation from the pulley to the feed roller occurs. The feed roller pulley is larger in diameter than the print roller pulley.

A "paper out" sensor is placed before the feed and snub rollers along the paper path. The "paper out" sensor includes a light emitter and an opposed corresponding detector. The paper passes between the emitter and detector. In addition to being used in the loading sequence of the recorder, the "paper out" sensor indicates, as is common for such sensors, that there is no longer paper in the recorder. In addition, a print head switch is placed near the print head to indicate whether the print head is in contact with the print roller. Both the "paper out" sensor and print head switch are preferably connected to a microprocessor.

Ideally, paper is used in the recorder having a series of black "dots" preprinted at a precisely determined positions on the back of the paper. The ink used in the "dots" is highly light absorptive. A "top of form" sensor is placed along the paper path to detect the passing of a black "dot" and alert the microprocessor.

The first step in loading the paper is to move the print head away from the print roller to an "open" position. This causes a signal to be sent to the microprocessor from the print head switch. Paper is then placed between the emitter and detector of the "paper out" sensor at the paper input causing a signal to be sent to the microprocessor from the "paper out" sensor. When the print head is away from the print roller and paper is present between the emitter and detector of the "paper out" sensor, a "load" condition is indicated.

In response to the "load" condition, the microprocessor directs the motor to run, causing the feed roller to rotate, until the second "top of form" is detected by the detection of the second black "dot". The black "dots" are located on the paper so that detection of the black "dots" by this sensor corresponds to the paper being positioned at the "top of form" position. Therefore, when the motor stops in response to the detection of the "dots", the paper is left at the "top of form" position.

In an alternate embodiment, the motor is directed to run until a predetermined amount of paper has passed through the recorder after a first "top of form" "dot" is detected. In another embodiment, the motor is directed to run for a preset length of time after the presence of paper is detected by the "paper out" sensor. In both these alternate embodiments, the microprocessor directs the motor to run for a preset amount of time which moves a corresponding length of paper through the recorder. In the first alternate embodiment, the preset time begins to run after the detection of the first "dot" while in the second alternate embodiment, the preset time begins to run upon the detection of paper by the "paper out" sensor. The preset time is chosen to move a length of paper through the recorder corresponding to the length of paper necessary to stop the "top of form" at a desired position. In these alternate embodiments, if a subsequent "dot" is detected, the motor stops thereby stopping the paper at the position determined by the location of the subsequently detected "dot" to be the "top of form".

The embodiment using a series of the "dots" to determine the location of the "top of form" of the paper is preferred to the embodiments using measurement of the time the motor runs to determine the "top of form" location because detecting a "dot" on each page stops the paper immediately on detection of the "dot". The only variability in the "top of form" location in this embodiment comes from the recorder's ability to precisely detect the black "dot" and then stop the motor. Experience has shown that it is fairly easy to precisely detect the "dot" and immediately stop the motor. Because a "dot" is detected on each page of the paper, no cumulative errors in locating the position of the "top of form" occurs.

In the alternate embodiments, cumulative errors may arise because the system for determining the location of the "top of form" is isolated from the actual location of the paper in the recorder. Therefore, if for example, the paper slips slightly on the print roller as it is pulled through the recorder, the actual location of the "top of form" will vary somewhat from the predicted location as determined by running the motor for the preset time.

Because the snub roller is in contact with the feed roller as the feed roller rotates, the snub roller rotates in the opposite direction of the feed roller. This rotation of the feed and snub rollers passes the paper between the feed and snub rollers, through the curved paper guide and between the print roller and the open print head.

After the second "top of form" is detected or a predetermined amount of paper has been passed through the recorder after the detection of the first "top of form" or after the preset time has expired, as appropriate, the motor stops. As a result of the motor running until directed to stop, a preset amount of paper has been passed through the recorder. This positions the paper within the recorder at the second "top of form" or otherwise as desired. The user then moves the print head into a "closed" position where the print head is in contact with the paper on the print roller. Moving the print head into the "closed" position activates the print head switch and alerts the microprocessor that the print head is in position to print on the paper.

The chart recorder also includes a drag inducing mechanism to impart tension to the paper as it passes through the guide structure of the chart recorder. It is important to impart drag to the paper to cause the paper to come into contact with the inner guide surface which helps to precisely position the paper at the print head. The inner guide surface has side walls or channels that come in contact with the edges of the paper to precisely position the paper within the paper guide prior to passing to the print head for printing. The drag inducing system includes the feed roller in contact with the snub roller.

When the paper is loaded and the print head closed, the paper contacts both the print and feed rollers; the print roller at one side of the paper guide and the feed roller at the other. As the print roller rotates when driven by the motor, the paper will be pulled through the recorder by frictional contact with the print roller. However, because the diameter of the pulley on the feed roller is larger than the diameter of the pulley on the print roller, the feed roller when driven by the motor tends to rotate at a slower rate than the print roller. But, because the paper contacts both the print and feed rollers as it passes through the recorder and because both rollers are identical in diameter, both rollers must rotate at the same speed if the paper is to pass through the recorder without sliding over the slower moving feed roller. Therefore, contact with the paper causes the feed roller to rotate faster than it is being driven by the motor through the feed roller pulley.

The one-way clutch allows the feed roller pulley to "free-wheel" around the feed roller at this slower rotational speed. While "free-wheeling", drag in the form of dissipative forces such as friction in the feed and snub roller bearings and the one-way clutch and friction due to contact with the feed and snub rollers is imparted to the paper through contact with the feed and snub rollers. This drag puts tension on the paper. The tension causes the paper to be drawn into tight contact with the inner guide surface allowing the paper to be precisely positioned by the side walls or channels of the curved inner guide to correctly align the paper for printing by the print head.

An additional feature of the recorder is a software "odometer" which effectively "measures" the length of paper passing through the recorder. The length of paper passing through the chart recorder is determined in the preferred embodiment by the microprocessor by multiplying the amount of time that the motor runs by the length of paper per unit time known to be passed through the recorder by the motor. The microprocessor uses this information to prevent passing excessive amounts of paper through the recorder and to allow the recorder to be used if the "top of form" sensor malfunctions or with paper not having the black "dots".

It is therefore an object of the instant invention to provide a chart recorder which will automatically load the paper upon which an ECG signal will be printed.

It is a further object of the instant invention to provide a chart recorder which precisely positions the paper to be printed including automatically sensing the "top of form" of the paper and positioning the paper accordingly and precisely aligning the paper with the print head.

It is an additional object of the instant invention to provide a drag inducing system for the chart recorder which causes the paper to be brought into contact with the guide structure of the chart recorder for precise positioning of the paper at the print head.

It is a further object of the instant invention to provide a chart recorder capable of measuring the length of paper passing through the chart recorder.

These and other objects of the invention will become clear with reference to the description contained herein and in particular in consideration of the following detailed description of the invention with reference to the accompanying drawings where identical elements are referred to by identical numbers.

BRIEF DESCRIPTION OF THE DRAWINGS

FIGS. 7A-C are side schematic views of one embodiment of the print head cover raising system of the instant invention.

DETAILED DESCRIPTION OF THE INVENTION

Figure 1A:
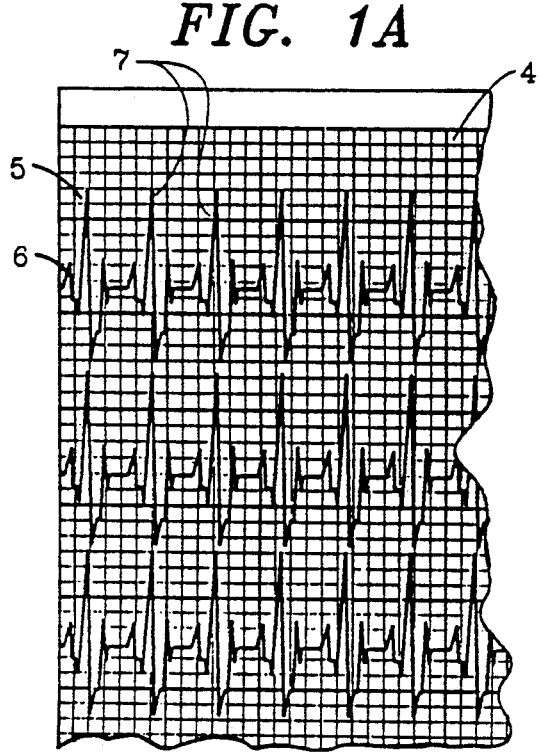
FIG. 1A is a plan view of the paper having preprinted grid lines and further showing ECG trace lines properly aligned with the preprinted grid lines.
Figure 1B:
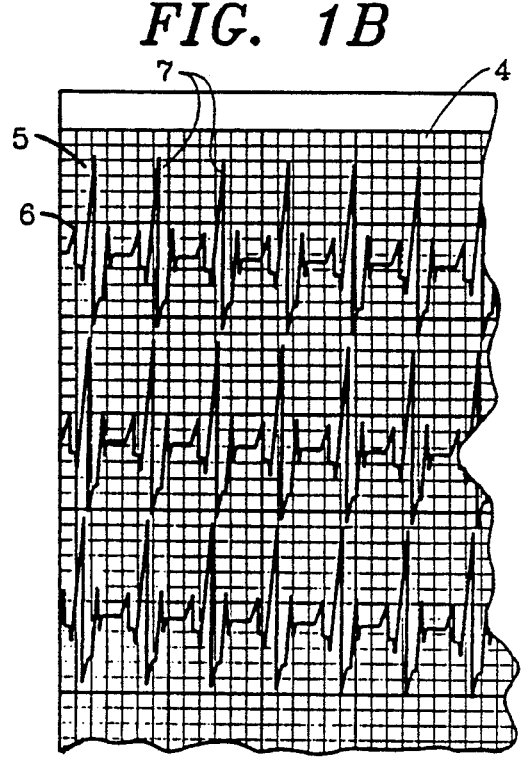
FIG. 1B is a plan view of the paper of FIG. 1A showing ECG trace lines misaligned with the preprinted grid lines.
Figure 6:
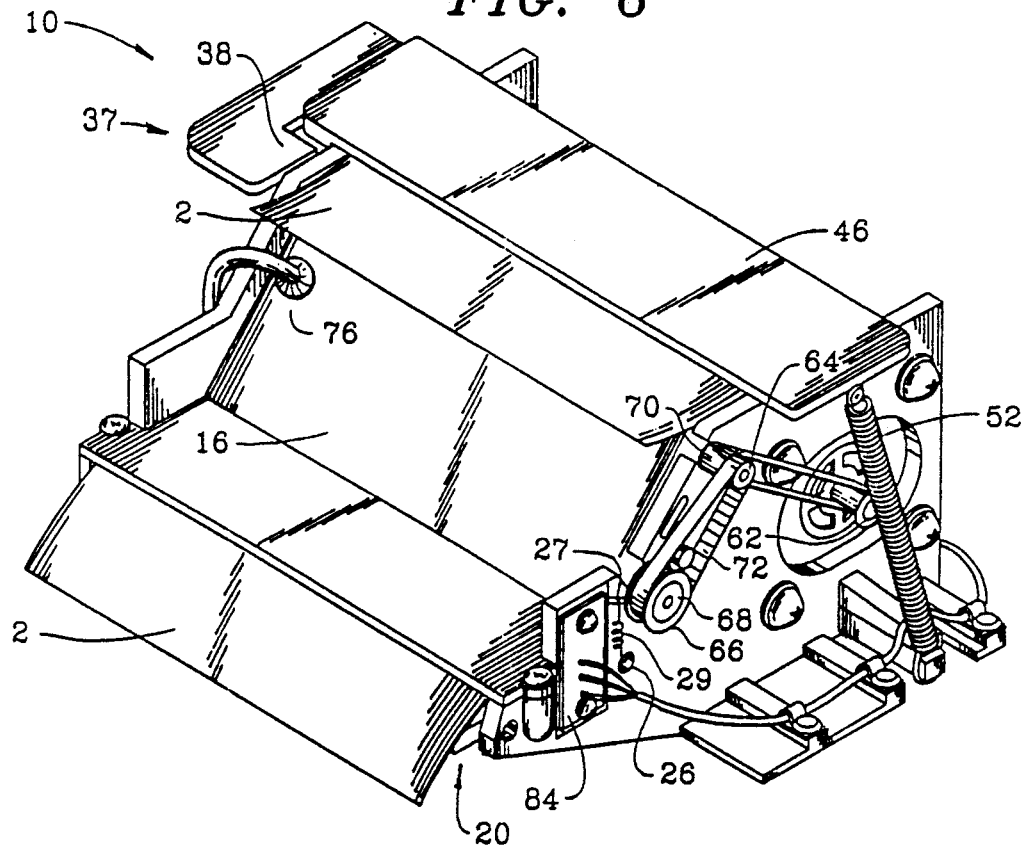
FIG. 6 is a perspective view of the assembled invention of FIG. 2.
Figure 2:
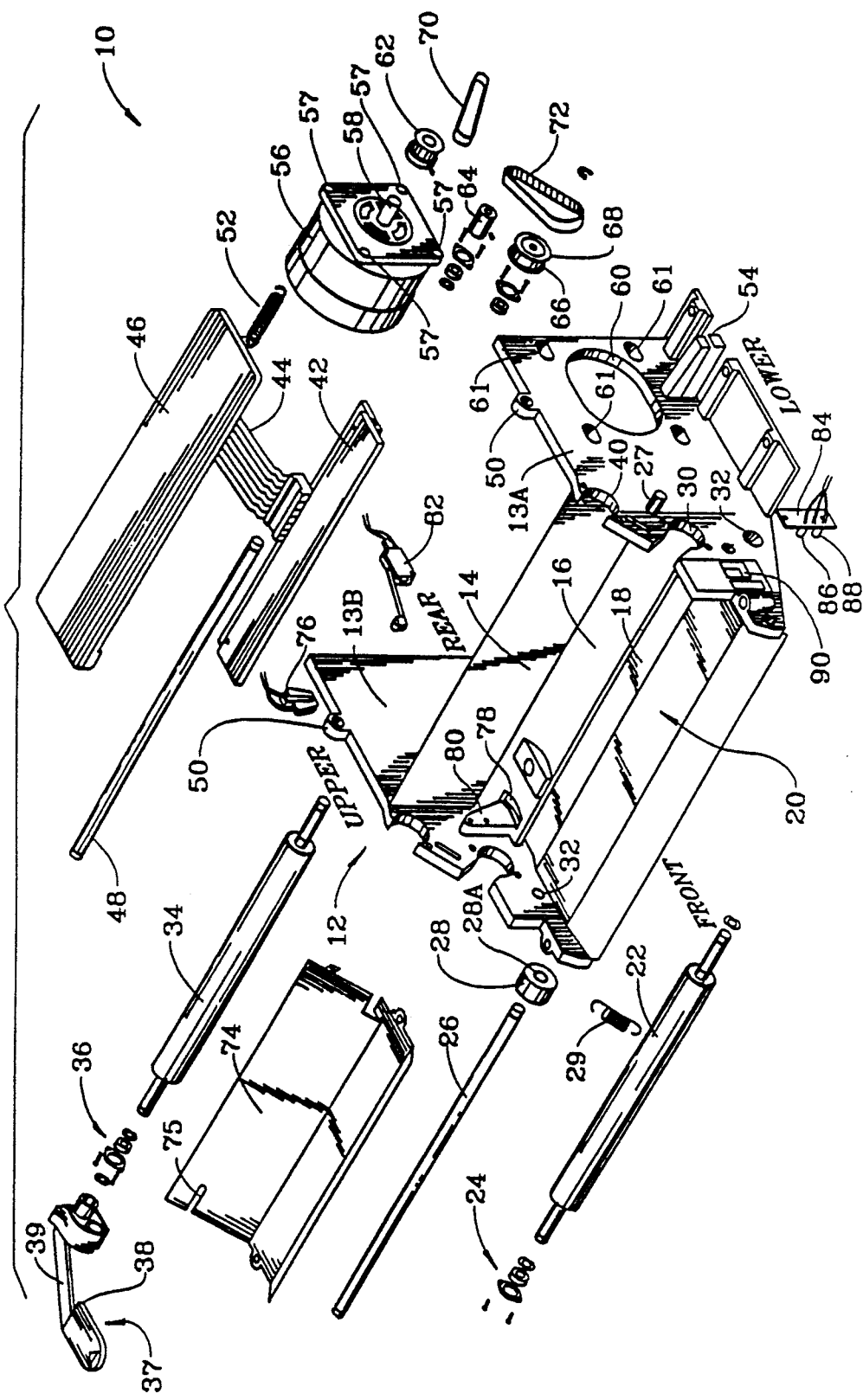
FIG. 2 is an exploded view of the invention.
Figure 3:
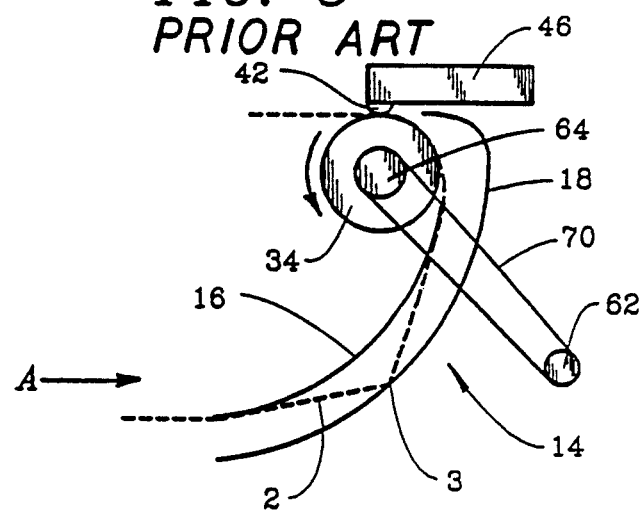
FIG. 3 is a side schematic view of a prior art invention showing the problem of the paper not contacting the inner surface of the paper guide.

With particular reference to FIGS. 2 and 6, the chart recorder is shown generally label 10. The chart recorder 10 includes a frame 12 comprising parallel opposing substantially planar side pieces 13a,b.

Figure 4:
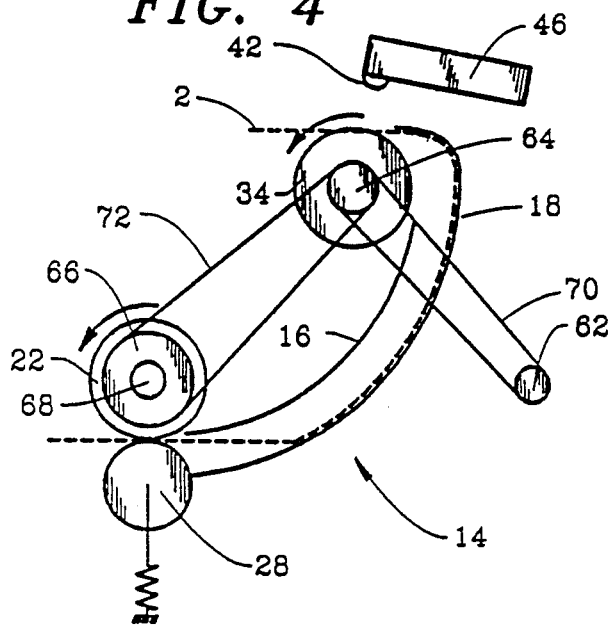
FIG. 4 is a side schematic view of the invention of FIG. 2 showing, the loading configuration of the invention.
Figure 5:
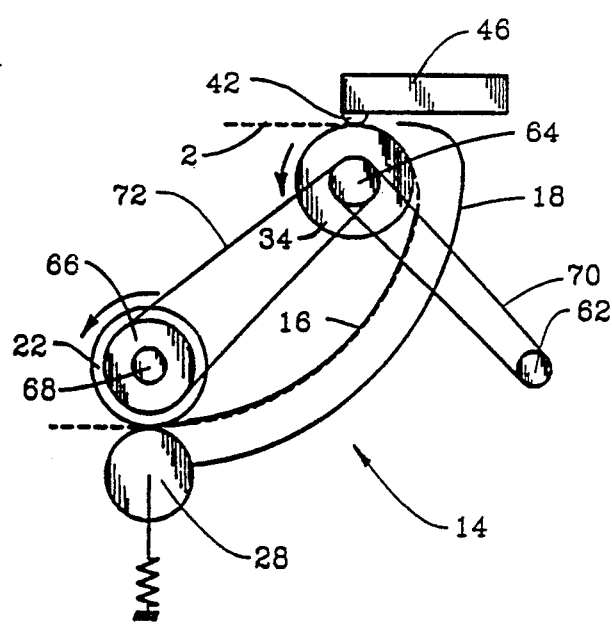
FIG. 5 is a side schematic view of the invention of FIG. 2 showing the paper loaded and ready for printing.

Frame 12 also includes a paper guide 14 located between side pieces 13a,b. The paper 2 to be printed is passed through paper guide 14 which positions the paper 2 for printing. As best seen in FIGS. 4 and 5, paper guide 14 has a curved inner guide 16 and a correspondingly curved outer guide 18. Inner and outer guides 16,18 extend between side pieces 13a,b with a constant separation which allows paper 2 to pass therebetween. Paper guide 14 extends from about the area of the lower part of chart recorder 10 near the front of the recorder 10 to the upper area of side pieces 13a,b for positioning of the paper 2 for printing as will be explained hereafter.

In this description, "front" and "rear" refers to the parts of chart recorder 10 commonly referred to as "front" and "rear" and generally labeled "front" and "rear" respectively in FIG. 2. In addition, throughout this description, "upper" and "lower" refers to the parts of chart recorder 10 commonly referred to as "upper" and "lower" and generally labeled "upper" and "lower" in FIG. 2. Also positioned between side pieces 13a,b is a paper input 20 which comprises a part of frame 12. Paper input 20 is a support surface for paper 2 which extends from the front of the chart recorder 10 to paper guide 14.

Side pieces 13a,b, paper guide 14 and paper input 20 are preferably die cast aluminum pieces having tolerances of ±0.002 inch. Die cast construction and the precise tolerances allow the pieces of the frame 12 to be precisely positioned as well as precisely positioning the additional elements of chart recorder 10 which will be attached to the frame pieces. Precise positioning helps to eliminate many printing misalignment problems.

Chart recorder 10 also includes a cylindrical feed roller 22 having flanged feed roller bearings 24 on each end. Feed roller bearings 24 are mounted in feed roller journals 30 precisely positioned on side pieces 13a,b near the front of paper guide 14 so that feed roller 22 extends between side pieces 13a,b. Feed roller journals 30 are located so that the bottom surface of feed roller 22 is approximately level with the upper surface of paper input 20. This allows paper placed on the surface of paper input 20 and pushed toward paper guide 14 to just contact the lower surface of feed roller 22.

A snub roller shaft 26 is provided having a snub roller wheel 28 positioned coaxially along its length. Snub roller wheel 28 is attached to snub roller shaft 26 by a bushing 28A which allows snub roller wheel 28 to rotate freely around snub roller shaft 26. Snub roller shaft receiving slots 32, positioned in side pieces 13a,b, constrain snub roller shaft 26 through contact with the ends of snub roller shaft 26. Snub roller shaft receiving slots 32 are located in side pieces 13a,b approximately below feed roller journals 30 so that snub roller shaft 26 extends between side pieces 13a,b. Feed roller 22 and snub roller shaft 26, when positioned between side pieces 13a,b are parallel to each other.

A spring 29 is provided on the outside of both side pieces 13a,b. Each spring 29 is attached at one end to the respective end of snub roller shaft 26 and at its other end to a respective snub roller spring retaining post 27 on side pieces 13a,b. Springs 29 bias snub roller shaft 26 toward feed roller 22. When snub roller shaft 26 is positioned in snub roller receiving slots 32, spring 29 biases snub roller wheel 28 into contact with feed roller 22.

The leading edge of paper 2 presented at paper input 20 and pushed toward paper guide 14 will then contact both feed roller 22 and snub roller wheel 28 as it passes between feed roller 22 and snub roller wheel 28. A single snub roller wheel 28 is provided instead of a series of snub roller wheels or a snub roller having a constant diameter without a separate snub roller wheel. The use of a single snub roller wheel 28 helps to prevent creasing of the paper passing between snub roller wheel 28 and feed roller 22. The single snub roller wheel 28 also facilitates steering of the paper 2 in the machine because it allows the paper 2 to pivot within the chart recorder 10 in response to the positioning systems described herein without substantial frictional resistance or binding. The snub roller wheel 28 used in the preferred embodiment of the chart recorder 10 is ½" wide and ¾" in diameter.

Where there is contact along a substantial part of the feed roller 22 and either a large snub roller wheel, several snub roller wheels, or a cylindrical snub roller itself, creasing of the paper 2 is caused by misalignment, imprecise positioning or imprecise manufacturing of feed roller 22 and the snub roller wheel or wheels or the cylindrical snub roller. Further, improper alignment of paper 2 as it is loaded can cause creasing. Any of these factors can cause the paper to bunch up prior to passing between the feed roller and the wheel or snub roller. This bunched up paper gets "pressed" or creased as it passes between the feed roller 22 and snub roller wheel or wheels, or the cylindrical snub roller. The more surface on the snub roller wheel or wheels or cylindrical snub roller that contacts feed roller 22, the more likely it is that creasing will occur.

A cylindrical print roller 34 having flanged print roller bearings 36 at each end is included in the chart recorder 10. Both print roller 34 and feed roller 22 have the same diameter in the preferred embodiment. Both rollers are preferably made of a neoprene coating around a steel shaft. The rollers are frozen, then machined to a precise diameter. In order to avoid creasing or uneven tension on the paper, a tolerance of plus or minus 0.005" in the diameter of the rollers is preferably maintained along the entire length of both rollers. Print roller bearings 36 on each end of print roller 34 are mounted in print roller journals 40 near the upper part of side pieces 13a,b to position print roller 34 therebetween.

A print head handle 37 is attached to and extends beyond the print roller bearing 36 of side piece 13b. Print head handle 37 rotates independently around the print roller bearing 36 located in side piece 13b. An elongated egg-shaped cam 39 extends away from the connection point of print head handle 37 and print roller bearing 36 so that the more pointed end of cam 39 extends in the same direction as print head handle 37 along a radial extending from the central axis of print roller 34. Print head handle 37 and cam 39 point in the same direction so that when print head handle 37 is parallel to the horizon, the more pointed part of cam 39 is also directed parallel to the horizon. Conversely, when print head handle 37 is moved to a substantially vertical position, the more pointed part of cam 39 also points in a substantially vertical direction.

A thermal print head 42, such as is common in the art, is provided for printing on paper 2. Preferably, print head 42 prints with a resolution of 8 dots/mm across the paper 2 and 10 dots/mm along the direction of paper travel although other resolutions or print heads of varieties other than those that print dots or use a thermal method of printing may be used as desired. Thermal print head 42 is controlled by an appropriate signal generating system, such as is known in the art, through a print head control cable 44. The signal generating system may include a microprocessor 92 (FIG. 11) or an ECG monitoring system.

A print head cover 46 attached to side pieces 13a,b through hinge rod 48 extending through journals 47 in print head cover 46. Hinge rod 48 is attached to and constrained between side pieces 13a,b through print head journals 50 located at the upper part of side pieces 13a,b. Print head 42 in turn is attached to print head cover 46 so that as print head cover 46 rotates around hinge rod 48 toward and away from print roller 34, print head 42 will also rotate toward and away from print roller 34.

Print head cover 46 extends beyond the edge of side piece 13b over cam 39. A protrusion 46A is attached to the lower surface of print head cover 46 at the point of contact with cam 39. Two springs 52 connect print head cover 46 with spring retaining apertures 54 at the lower part of side pieces 13a and b to bias print head cover 46 toward print roller 34. Because print head handle 37 and cam 39 point in the same direction, when print head handle 37 is parallel to the horizon, the elongated part 39A of cam 39 is parallel to the horizon so that protrusion 46A of print head cover 46 contacts the relatively narrow part 39B of cam 39 under the bias of spring 52. In this configuration, print head 42 is in its most downward or "closed" position and is in contact with paper 2 placed between print head roller 34 and print head 42 for printing on paper 2.

As print head handle 37 and cam 39 are rotated toward a vertical position, the elongated part 39A of cam 39 is brought into contact with the protrusion 46A which progressively raises print head cover 46 against the bias of spring 52. Raising print head cover 46 rotates print head 42 around hinge rod 48 away from print roller 34 and out of contact with any paper 2 that may be present.

Spring 52 is preferably located so that as print head cover 46 is raised by cam 39, spring 52 moves from a point of comparatively lower tension just as print head cover 46 is beginning to be raised through a position of high tension while being raised and ending finally at a position of slightly lower than maximum tension when print head cover 46 is raised to its highest or most "open" position.

In one embodiment, a stop 38 extends from print head handle 37 over print head cover 46. Stop 38 rotates into contact with the upper surface of print head cover 46 when print head cover 46 is raised by cam 39 to its highest or most "open" position by the rotation of print head handle 37. Contact between stop 38 and the upper surface of print head cover 46 prevents print head handle 37 from further rotating around print roller bearing 36.

In this embodiment, as shown in FIGS. 7A-C, cam 39 contacts protrusion 46A, which is a small curved protrusion on the lower side of print head cover 46. When print head cover 46 is in its most downward or "closed" position, the narrower part 39B of cam 39 contacts the curved protrusion 46A (FIG. 7A). As print head handle 37 is rotated around print roller bearing 36, cam 39 contacts the curved protrusion 46A at points progressively farther and farther along the elongated part 39A of cam 39. As print head handle 37 is rotated around print roller bearing 36, the elongated part 39A of cam 39 contacts the curved protrusion 46A and raises print head cover 46 against the bias of spring 52. Spring 52 biases print head cover 46 to move toward print roller 34 if print head handle 37 is released while raising print head cover 46.

As shown in FIGS. 7B and C, a line "B" extends from the center of print roller bearing 36 to print head cover 46 so that line "B" is perpendicular to print head cover 46. When the pointed end of the elongated part 39A of cam 39 contacts protrusion 46A at line "B" as shown in FIG. 7B, because of the narrow point of contact between the pointed end of the elongated part 39A of cam 39 and protrusion 46A, the bias of spring 52 on print head cover 46 causes cam 39 in this position to be in an unstable configuration. Slight movement of the more pointed end of cam 39 in a counterclockwise direction as viewed from FIG. 7B would cause cam 39 to continue to rotate in a counterclockwise direction under pressure from print head cover 46 due to the bias of spring 52 until print head cover 46 is stopped by contact between print head 42 and print roller 34.

On the other hand, slight movement of the pointed end of cam 39 in a clockwise direction as viewed from FIG. 7B would cause cam 39 to continue to rotate in a clockwise direction under pressure from print head cover 46 due to the bias of spring 52 until stop 38 contacts the upper surface of print head cover 46. When this occurs, print handle 37, and by extension cam 39, can no longer rotate in a clockwise direction. The bias of spring 52 puts pressure on cam 39 through contact between protrusion 46A and the part of cam 39 contacting protrusion 46A (FIG. 7C). This pressure is transferred through print handle 37 to stop 38 and ultimately to the upper surface of print head cover 46 so that stop 38 is jammed against the upper surface of print head cover 46. This causes print head cover 46 to remain in a relatively open position away from print roller 34.

Figure 8:
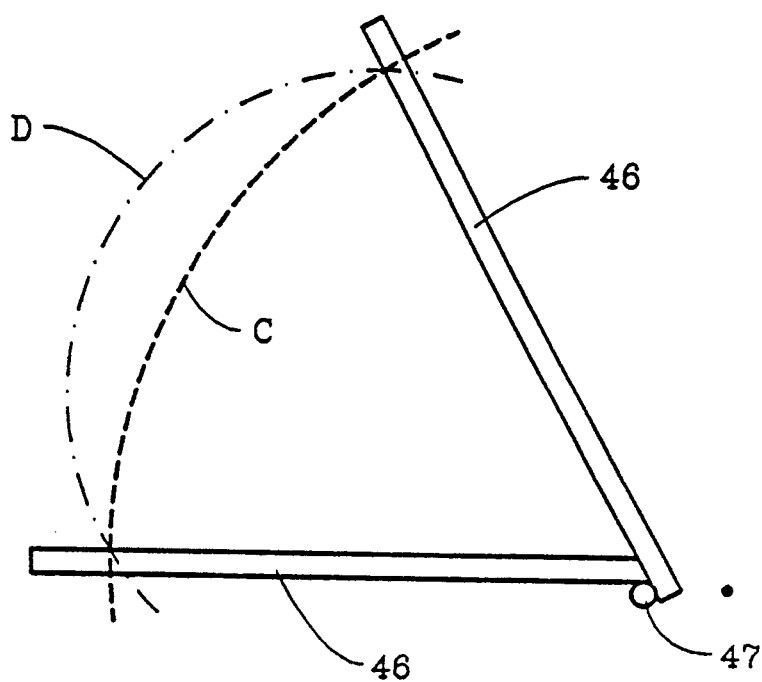
FIG. 8 is a side schematic view of another embodiment of one part of the print head cover raising system of the instant invention.

Another embodiment for holding print head cover 46 open is shown in FIG. 8. In this embodiment the system for raising the print head cover 46 comprising print handle 37, cam 39 and protrusion 46A is exactly the same as described above with the exception that no stop 38 is used. In FIG. 8, arc "C" is an arc representing equal tension on spring 52 as spring 52 rotates around aperture 54 in response to the movement of print head cover 46. Arc "D" is an arc drawn by the rotation of the point of attachment of spring 52 to print head cover 46 as print head cover 46 rotates around hinge rod 48. Aperture 54 is located on side piece 13a so that arc "C" intersects arc "D" at both the fully raised or "open" and lowered or "closed" positions of print head cover 46.

In the fully raised or open position, the gravitational force on print head cover 46 and print head 42 will cause print head cover 46 to tend to fall toward the closed position. Spring 52 is chosen to provide a return force which precisely counters the gravitational force so that print head cover 46 remains suspended at the "open" position. In this way, spring 52 biases print head cover 46 toward print roller 34 during the print operation and also holds print head cover 46 in an open position when it is raised to its highest position.

In either embodiment, holding the print head cover 46 in an open position allows the paper 2 to pass between print head 42 and print roller 34. In addition, holding the print head cover 46 open allows access to print head 42 so that it may be easily cleaned. Further, print head cover 46 itself may be manually moved to and from an "open" and "closed" position without using the print handle 37 and cam 39 described above.

A motor 56 is provided having an extended rotating shaft 58. In the preferred embodiment, motor 56 is attached to side piece 13a so that shaft 58 extends through a motor aperture 60 in side piece 13a. Motor 56 is attached to side piece 13a by screws extending through motor mounting apertures 61 into threaded recesses 57 on motor 56. Motor 56 is preferably a two phase stepping motor run by a microstepping power driver which can be controlled to rotate at a predetermined precise speed. Motor 56 powers the passage of paper 2 through the chart recorder 10. The AAMI has set precise standards for the allowed variability in the rate of paper passage through chart recorders in order to ensure accurate recording of the ECG signals. Therefore, it is important that motor 56 maintains a precise rotational speed in order to meet these standards.

A motor pulley 62 is collinearly attached to the end of shaft 58 outside of frame piece 13a. A print roller pulley 64 is attached to the end of print roller 34 outside of frame piece 13a. Motor pulley 62 and print roller pulley 64 are aligned to be in approximately the same plane so that a print roller belt 70, which is preferably a rubber timing belt, connects motor pulley 62 and print roller pulley 64. Rotation of motor pulley 62 causes print roller pulley 64 to rotate in the same direction. Print roller pulley 64 is an elongated pulley having sufficient width to allow two roller belts to be attached to it side-by-side.

In an alternate embodiment, motor 56 may be attached directly to print roller 34 along shaft 58. In this embodiment, there is no motor pulley 62. As motor 56 rotates shaft 58, print roller 34 and print roller pulley 64 also rotate.

In either embodiment, a feed roller pulley 66 is collinearly mounted around a one-way clutch 68. One-way clutch 68 is in turn collinearly attached to the end of feed roller 22. A feed roller belt 72, which is preferably a rubber timing belt, connects print roller pulley 64 to feed roller pulley 66 so that rotation of print roller pulley 64 causes feed roller pulley 66 to rotate in the same direction. Feed roller pulley 66 is preferably larger in diameter than print roller pulley 64 so that a single rotation of print roller pulley 64 causes less than a complete rotation of feed roller pulley 66. In the preferred embodiment, feed roller pulley 66 has 34 teeth while print roller pulley 64 has only 24 similarly sized teeth.

One-way clutch 68 is preferably of the type known as a "Sprag clutch" although other types of one-way clutches may be used. One-way clutch 68 allows feed roller pulley 66 to rotate freely or "free wheel" in a clockwise direction relative to feed roller 22. Throughout this description, the directions of rotation are as seen from outside side piece 13a unless specifically stated otherwise. Clutch 68 transfers counterclockwise rotation of feed roller pulley 66 to feed roller 22 causing the feed roller 22 to rotate in a counterclockwise direction if the relative rotation of feed roller pulley 66 to feed roller 22 is not clockwise.

It is important to note that the directions of rotation referred to herein are relative. For example, feed roller pulley 66 rotates in a clockwise direction relative to feed roller 22 both when feed roller 22 is stationary and feed roller pulley 66 rotates in a clockwise direction as explained above and when feed roller pulley 66 is held stationary and feed roller 22 rotates in a counterclockwise direction.

Further, if both feed roller 22 and feed roller pulley 66 are rotating in a counterclockwise direction, the relative direction of rotation must be ascertained to determine whether rotation of feed roller pulley 66 is transferred to feed roller 22. For example, if both feed roller pulley 66 and feed roller 22 are rotating in a counterclockwise direction, but feed roller pulley 66 is rotating at a slower rate than feed roller 22, feed roller pulley 66 is rotating in a clockwise direction relative to feed roller 22.

Counterclockwise rotation of print roller pulley 64 causes counterclockwise rotation of feed roller pulley 66. As long as feed roller pulley 66 does not rotate in a clockwise direction relative to feed roller 22, one-way clutch 68 transfers the counterclockwise rotation of feed roller pulley 66 to feed roller 22 causing feed roller 22 to rotate in a counterclockwise direction.

As stated above, when print roller pulley 64 rotates in a counterclockwise direction, feed roller pulley 66 also rotates in a counterclockwise direction. Also as explained above, because feed roller pulley 66 is larger in diameter than print roller pulley 64, feed roller pulley 66 will rotate at a slower rate than print roller pulley 64. However, for reasons that will be explained hereafter, during the operation of the chart recorder 10, while motor 56 is driving print roller pulley 64 and consequently feed roller pulley 66 in a counterclockwise direction, feed roller 22 will also be independently rotated in a counterclockwise direction at a faster rotational rate than feed roller pulley 66 is being rotated. When this occurs, feed roller pulley 66 is rotating in a clockwise direction relative to feed roller 22. This relative clockwise rotation causes feed roller pulley 66 to "free wheel" around clutch 68 so that its rotation is not imparted to feed roller 22. In other words, in this case, feed roller 22 rotates in its counterclockwise direction completely unaffected by the slower counterclockwise rotation of feed roller pulley 66.

Figure 9:
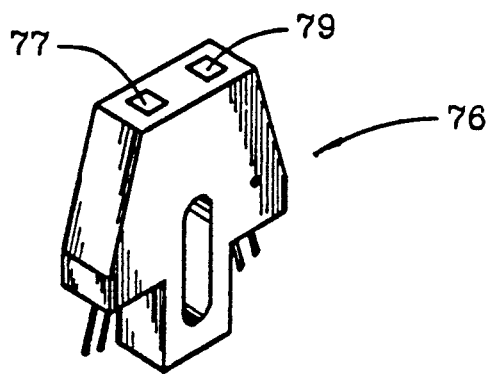
FIG. 9 is a perspective view of the top of form sensor.

A top of form sensor 76 is provided as shown in FIG. 9. Top of form sensor 76 includes a light emitter 77 and a light detector 79. Emitter 77 is preferably an infrared light emitting diode (IRLED) while detector 79 is preferably a photodiode sensitive to infrared light. In the preferred embodiment, both emitter 77 and detector 79 are encased in a single unit, as shown in FIG. 9, such as that manufactured by the TRW Electronic Components Group as Type OPB703A. Detector 79 is connected to the microprocessor 92 or other control means.

Infrared emitters and detectors are preferably used instead of visible light emitters and detectors to minimize unintentional detection by detector 79 of the ambient visible light. However, both emitter 77 and detector 79 may be of the visible light variety if additional electronic circuitry or shielding is used to minimize accidental detection of ambient visible light. In this case, emitter 77 may be a light emitting device such as a visible light LED or incandescent bulb. Detector 79 may be any device which is able to detect the light emitted from emitter 77 such as phototransistors, photocells or solar-cells. If visible light detectors and emitters are to be used, the additional electronic circuitry which minimizes the accidental detection of ambient visible light could include circuitry which pulses the emitter and synchronously detects the pulsed emitted light. Such pulsing and detecting circuitry are well known in the art.

A sensor aperture 78 extends through inner guide 16 below a sensor mounting post 80 on inner guide 16. Sensor 76 is attached to sensor mounting post 80 above sensor aperture 78 so that the light emitted from emitter 77 passes downward through sensor aperture 78 into the space between inner and outer guides 16, 18. The use of top of form sensor 76 will be explained hereafter.

A print head switch 82 is attached to side piece 13b below print head cover 46. Print head switch 82 is preferably a contact switch which is normally closed. When print head cover 46 is moved downward into the "closed" position, print head 42 is moved into a printing position. When this occurs, print head cover 46 contacts switch 82 thereby causing it to close. The closed switch 82 allows electrical current to pass through it is detected by appropriate means such as microprocessor 92 thereby indicating that print head 42 is in position to print.

When print head cover 46 is rotated around hinge rod 48 away from print roller 34 into the "open" position, print head cover 46 is moved out of contact with print head switch 82 thereby opening switch 82 and preventing the flow of electrical current. This indicates to microprocessor 92 or other control means that print head 42 is not in position to print. The use of print head switch 82 in chart recorder 10 will be described in detail hereafter.

Figure 10:
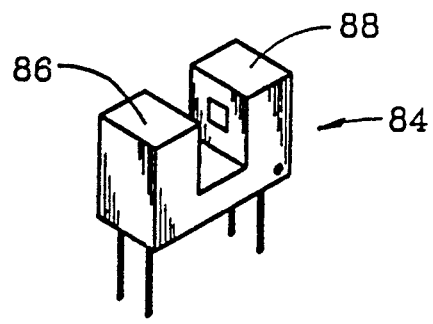
FIG. 10 is a perspective view of the paper out sensor.

A paper out sensor 84 is also provided as shown in detail in FIG. 10. Paper out sensor 84 includes an emitter 86 and a detector 88, both extending away from paper out sensor 84 in an essentially "U" shaped configuration. The "U" shaped configuration of paper out sensor 84 has emitter 86 located on one arm of the "U". Light emitted from emitter 86 is directed toward the other arm of the "U" shaped sensor 84 which contains the detector 88. Emitter 86 is preferably an infrared light emitting diode (IRLED) while detector 88 is preferably a photodiode sensitive to infrared light. Detector 88 is connected to microprocessor 92 or other appropriate signal processing means.

For similar reasons to those given in connection with the top of form sensor 76, emitter 87 and detector 88 are preferably of the infrared variety but could be of the visible light type with appropriate measures, as explained in connection with the top of form sensor 76, to minimize the possibility of accidental detection of ambient visible light. When the emitter 87 and detector 88 are of the visible light type, emitter 86 may be a light emitting device such as a visible light LED or incandescent bulb, while detector 88 may be any corresponding device which is able to detect the light emitted from emitter 86 such as phototransistors, photocells, or solar-cells.

Paper out sensor 84 is placed through a sensor aperture 90 in the side piece 13a near paper input 20 so that paper presented at paper input 20 will pass between emitter 86 and detector 88. When no paper 2 is present at paper input 20, light from emitter 86 is detected by detector 88. When paper 2 is present at paper input 20, the paper 2 passes between emitter 86 and detector 88. In this configuration, light emitted from emitter 86 is absorbed by paper 2 and is no longer detected by detector 88. This indicates to microprocessor 92 that paper 2 is present at paper input 20.

In chart recorder 10, paper 2 is used preferably having preprinted grid lines on one side extending in both the horizontal and vertical direction. Paper 2 also preferably contains a series a preprinted black "dots", preferably made of a light absorptive material, located on the side of paper 2 opposite the preprinted grid lines for a purpose which will be described hereafter.

In operation, paper 2 is manually presented at paper input 20 for loading into the chart recorder 10. As the paper 2 is pushed into paper input 20, it passes between emitter 86 and detector 88 of paper out sensor 84. Because light emitted from emitter 86 is absorbed by paper 2, detector 88 no longer detects the light. This is detected by microprocessor 92 and indicates the presence of paper 2 at paper input 20.

Microprocessor 92 then determines whether print head 42 is not in contact with the print roller 34 as indicated by print head switch 82. In order to be in the "load" mode, paper 2 must be presented at the paper input 20 and print head 42 must be rotated away from print roller 34 by the interaction of cam 39 with print head cover 46 or by manual action, as described above. When both the sensor 84 indicates that paper is present at paper input 20 and print head switch 82 indicates that the print head 42 is out of contact with print roller 34, microprocessor 92 initiates the loading sequence.

The loading sequence consists of the microprocessor 92 directing motor 56 to rotate in a counterclockwise direction until the second "top of form" "dot" has been detected, a preset time has expired after the detection of a first "top of form" "dot", or after a preset time has expired after the "paper out" sensor 84 has indicated the presence of paper 2 as explained above. The rotation of motor 56 causes motor pulley 62 to rotate which in turn causes print roller pulley 64 to rotate in the counterclockwise direction. Rotation of print roller pulley 64 in turn causes feed roller pulley 66 to rotate in a counterclockwise direction.

When feed roller pulley 66 first begins rotating in the counterclockwise direction, feed roller 22 is not rotating at all so feed roller pulley 66 is clearly not rotating in a clockwise direction relative to feed roller 22. As a result, one-way clutch 68 causes feed roller 22 to also rotate in the counterclockwise direction in response to the rotation of feed roller pulley 66. This rotation of feed roller 22 causes the paper presented at paper input 20 to be passed between feed roller 22 and snub roller wheel 28 due to frictional contact between the paper 2 and the rotating feed roller 22. Motor 56 preferably rotates at a rate causing paper 2 to be passed between feed roller 22 and snub roller wheel 28 at a rate of 25 mm/sec.

As feed roller 22 continues to rotate, paper 2 is passed into paper guide 14 between inner guide 16 and outer guide 18 as best shown in FIG. 4. Paper 2 typically contacts outer guide 18 which guides paper 2 in an upward direction toward print head 42 and print roller 34. Paper guide 14 is curved a sufficient amount to direct the paper exiting paper guide 14 at its upper end back toward the front of chart recorder 10. Because print head 42 has been moved out of contact with print roller 34, paper 2 passing out of paper guide 14 is able to pass between print head 42 and print roller 34.

As mentioned above, during the loading sequence, motor 56 is directed by microprocessor 92 to run until a predetermined length of paper 2 has passed through the recorder 10 as explained above. This predetermined length is chosen so that feed roller 22 will continue to rotate, thereby passing paper 2 through paper guide 14, for a time sufficient to allow the leading edge of paper 2 to pass between print head 42 and print roller 34 and so that paper 2 will be positioned in chart recorder 10 at the "top of form" position.

When the predetermined length of paper 2 has been passed through the recorder 10 or if the user closes print head 42 prior to the predetermined length of paper 2 passing through the recorder 10, motor 56 ceases to run. If it has not already been moved to stop motor 56 from running as explained above, print head handle 37 is manually rotated downward thereby causing print head cover 46 to move toward print roller 34 into the "closed" position. Spring 52 biases print head cover 46 toward print roller 34 so that print head 42 comes in secure contact with paper 2 on print roller 34. The bias of spring 52 on print head cover 46 causes the print head switch 82 to be depressed indicating to microprocessor 92 that print head cover 46 is now in the "closed" position. In addition, because paper 2 is present in chart recorder 10, paper out sensor 84 reports to microprocessor 92 that paper 2 is present.

As a result of microprocessor 92 determining that print head 42 is in contact with print roller 34 and paper is present in the recorder lo, microprocessor 92 initiates a sequence to secure paper 2 within paper guide 14 to properly position paper 2 preparatory to passing between print roller 34 and print head 42. This positioning is done by a tension producing system where microprocessor 92 directs motor 56 to rotate in the counterclockwise direction thereby causing both print roller pulley 64 and feed roller pulley 66 to rotate in the counterclockwise direction. Because of frictional contact between print roller 34 and paper 2 as the paper 2 passes over print roller 34, rotation of print roller 34 will impart movement to paper 2 so that paper 2 will be pulled from paper input 20 through paper guide 14 by print roller 34. The neoprene coating on print roller 34 allows print roller 34 to pull paper 2 without slipping so that the speed of the rotation of the circumference of print roller 34 is equal to the speed of paper 2 as it passes through chart recorder 10.

As mentioned above, feed roller pulley 66 is larger than print roller pulley 64. As a result, as print roller pulley 64 rotates, feed roller pulley 66 will rotate at a slower rotational speed than print roller pulley 64. However, as paper 2 passes between feed roller 22 and snub roller wheel 28, frictional contact between paper 2 and the neoprene coating on feed roller 22 will cause feed roller 22 to rotate as paper 2 is pulled through paper guide 14 by the rotation of print roller 34. Because feed roller 22 and print roller 34 have the same diameter, if the paper 2 is to pass by feed roller 22 without slipping, feed roller 22 must rotate at the same rate as print roller 34.

The speed of rotation of feed roller 22, due to its frictional contact with paper 2 as paper 2 is pulled through the recorder 10 by print roller 34, is a faster rotation than the rotation imparted to feed roller 22 through rotation of feed roller pulley 66 by motor 56. The relative effect of these different rotational speeds is that feed roller pulley 66 is rotating in a clockwise direction relative to feed roller 22. Because of this relative clockwise rotation, one-way clutch 68 allows feed roller pulley 66 to "free-wheel" around feed roller 22. The net result is that although feed roller pulley 66 is rotating, its rotation is not being imparted to feed roller 22.

Because there are dissipative forces such as friction in feed roller bearings 24, as well as frictional forces in the rotation of the snub roller wheel 28 around snub wheel bearing 28A and friction between snub wheel 28 and paper 2, both feed roller 22 and snub roller wheel 28 will have some resistance to rotation. In particular, feed roller 22 and snub roller wheel 28 will resist rotating due to frictional contact with the paper 2 being pulled by print roller 34. This resistance to rotation of feed roller 22 and snub roller wheel 28 causes tension to be imparted to paper 2 within paper guide 14. That is, paper 2 is pulled at one end of paper guide 14 by print roller 34 while paper 2 is resisting being pulled at the other end of paper guide 14 by the resistance to rotation of feed roller 22 and snub roller wheel 28. This tension causes paper 2 to be pulled towards inner guide 16 which, as mentioned, has precisely positioned edge guides or channels for receiving and aligning paper 2 with print head 42. Consequently, paper 2 will be precisely positioned within paper guide 14.

The tension producing system described above provides tension on paper 2 for precisely positioning paper 2 on inner guide 16 both during the process to locate the "top of form" of paper 2 and during the normal printing operation of chart recorder 10. During normal printing operation, paper 2 is moved through the chart recorder 1 by the rotation of print roller 34 as described above.

The tension producing system described above in connection with the process to locate the "top of form", during normal printing operations, imparts tension to paper 2 as described above simultaneously while paper 2 is moved through the chart recorder 10 by the rotation of print roller 34. The tension imparted to paper 2 by the tension producing process pulls paper 2 into secure contact with inner guide 16 for precisely positioning paper 2 prior to passing paper 2 to print head 42 for printing.

The edge guide or channels for receiving and aligning paper 2 within paper guide 14 may be the side pieces 13a,b themselves or may be recessed channels in the inner guide 16. In either case, because of the requirement that the side pieces 13a,b or channels be separated by the width of the paper 2 plus a nominal tolerance, the chart recorder 10 is manufactured for use with paper 2 having a specific width. As a result, different versions of chart recorder 10 may be made to accommodate varying widths of paper 2 commonly used such as paper with a 8½" width or A4 size paper.

As can be seen with reference to FIG. 5, the side of paper 2 in contact with inner guide 16 is the opposite side of paper 2 that will be printed on by print head 42. As previously mentioned, paper 2 is used preferably having preprinted black "dots" of a light absorptive material. These "dots" are placed on the back of paper 2 so that they pass under sensor aperture 78 in inner guide 16. In this way, the light emitted by emitter 77 of sensor 76 is emitted downward through sensor aperture 78 to paper 2. Ordinarily, this emitted light will be reflected by paper 2 back toward detector 79 in sensor 76.

When one of the black "dots" passes beneath sensor aperture 78 as paper 2 is passed through recorder 10, the light emitted by emitter 77 is absorbed by the black "dot" so that detector 79 ceases to detect the emitted light. When this happens, in the preferred embodiment, microprocessor 92 directs motor 56 to continue running until the next black "dot" is found. When the second "dot" is found, microprocessor 92 directs the motor 56 to cease rotation thereby stopping the paper in position within chart recorder 10. These black "dots" are preprinted and located on the back of paper 2 so that when motor 56 stops in response to the detection of the "dots", paper 2 will be precisely positioned at the "top of form" for printing by print head 42. Stopping paper 2 after the detection of the second "dot" allows a "leader" sheet of paper to precede the sheet of paper 2 which will actually receive the ECG trace. Of course, if desired, the "leader" sheet could be eliminated and the paper 2 positioned at the "top of form" position upon the detection of the first black "dot".

Once chart recorder 10 is operating to print ECG traces, as paper 2 is advanced through the recorder 10, the black "dots" are used to precisely position the new sheet of paper 2 at the "top of form" position prior to being printed on by print head 42. After the paper 2 has been precisely positioned at the "top of form" position, ECG signals may be printed on paper 2 by print head 42. As the ECG signals are printed, paper 2 is continuously advanced through recorder 10 so that the printing of the ECG signals on paper 2 represents the time varying nature of the ECG signals.

The paper 2 is advanced through chart recorder 10 by the counterclockwise rotation of print roller pulley 64 and consequently print roller 34. As explained above, the counterclockwise rotation of print roller 34 causes frictional contact with paper 2 which pulls paper 2 through the recorder 10. In the preferred embodiment, motor 56 has three rotational speeds which cause the paper 2 to be advanced through the recorder 10 at rates of 5, 25, and 50 mm/sec depending on the spread and resolution of the ECG signal desired.

The chart recorder 10 includes a software driven "odometer" which effectively "measures" the length of paper 2 passing through the recorder 10. The software is preferably implemented on microprocessor 92 which is connected to the "top of form" sensor 76 and the "paper out" sensor 84. The software also controls motor 56 through microprocessor 92. The source code of the software is attached hereto as Appendix I.

Basically, the software "measures" the amount of paper 2 passed through the chart recorder 10 by measuring the time that motor 56 runs as it passes paper 2 through the recorder 10 and then multiplying this length of time by the rate that the paper 2 passes through the recorder 10.

Microprocessor 92 uses this information for two purposes. First, after a preselected amount of paper 2 has been determined to have been passed through the recorder 10, microprocessor 92 determines whether a "top of form" has been indicated by the "top of form" sensor 76. The preselected amount of paper 2 is preferably slightly longer than the expected page length. A lack of a "top of form" indication may be caused by a faulty sensor, improper positioning of the paper, or from using paper without the preprinted black "dots". If no "top of form" has been indicated, microprocessor 92 turns motor 56 off to prevent passing excessive paper 2 through the recorder 10.

Second, if no "top of form" is indicated because of a faulty sensor or from using paper with no preprinted black "dots", and the user wants to use the recorder anyway, the paper 2 may be manually moved to the "top of form" position. Thereafter, the odometer "measures" the amount of paper passing through the recorder 10 and passes the information to microprocessor 92. After microprocessor 92 determines that a page length has passed, microprocessor 92 then stops the motor 56, which causes paper 2 to stop at the position determined to be on the "top of form" by measurement of the passed page length.

Experience has shown that the accuracy in measurement of the page length by this odometer is about 1.78%. This variation in positioning the paper 2 is known as "creep". Therefore, on a typical 11 inch page length, the maximum "creep", would be about 0.22 inch/sheet while the usual variation would typically be somewhat less.

Figure 11:
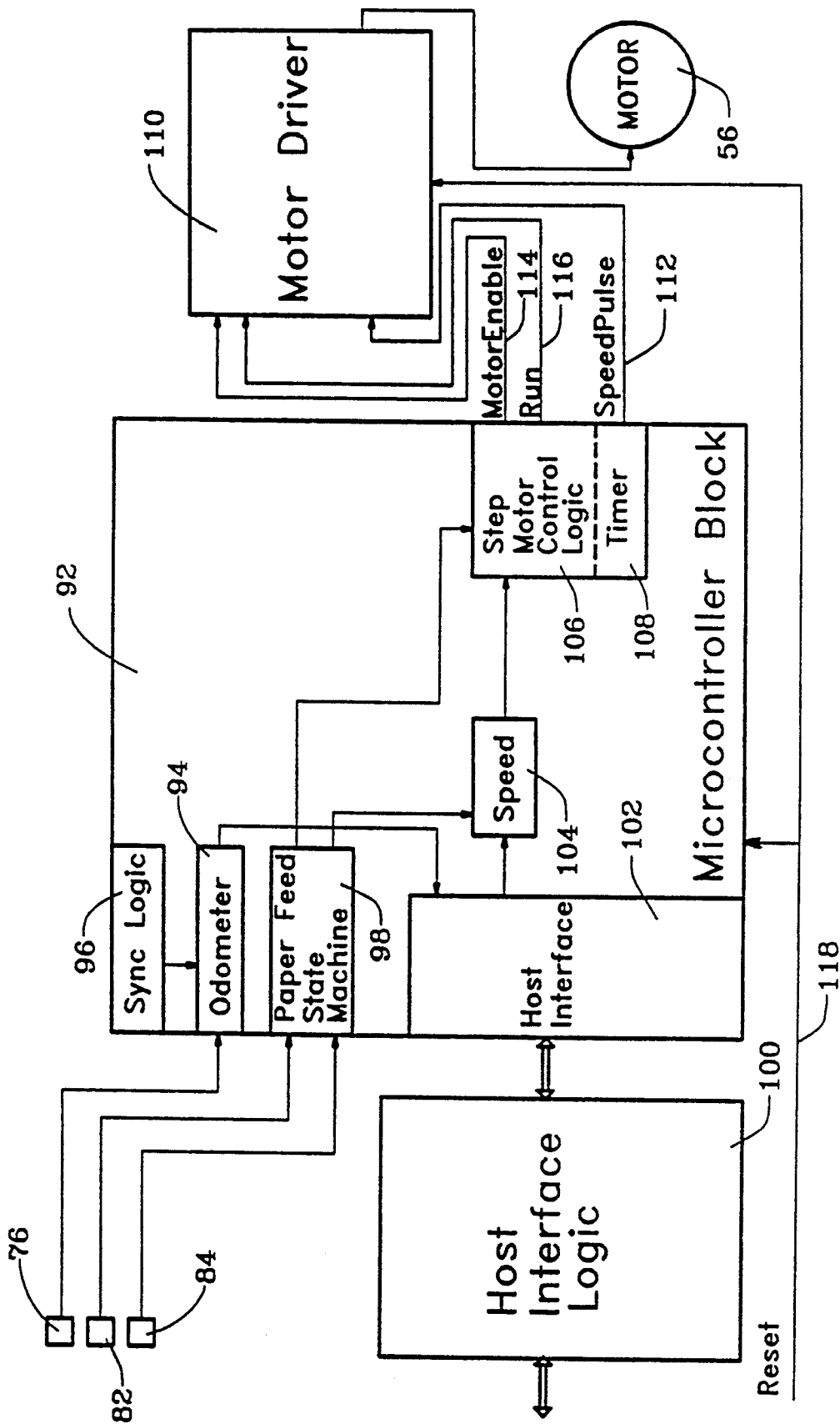
FIG. 11 is a block diagram of the electronic components and software modules of the instant invention.

A block diagram of the electronics and software modules of the instant invention is shown in FIG. 11. The microprocessor or microcontroller block is labeled 92. The microprocessor 92 is preferably a programmable microprocessor having onboard programmable timers and may be of the variety such as that made by Texas Instrument Company as Part No. TMS370C250. The top of form sensor 76, print head switch 82 and paper out sensor 84 are all connected to microprocessor 92.

Top of form sensor 76 is shown attached to microprocessor 92 at odometer module 94. Odometer module 94 is a software module which implements the odometer system described above. Since odometer module 94 is a software module, it is implemented by microprocessor 92 according to preprogrammed instructions such as those contained in Appendix I. Sync Logic module 96 is a timer software module, symbolically connected to odometer module 94, which times the amount of time that motor 56 runs and passes the amount of time to odometer module 94 for calculation of the page length as described above.

Figure 12:
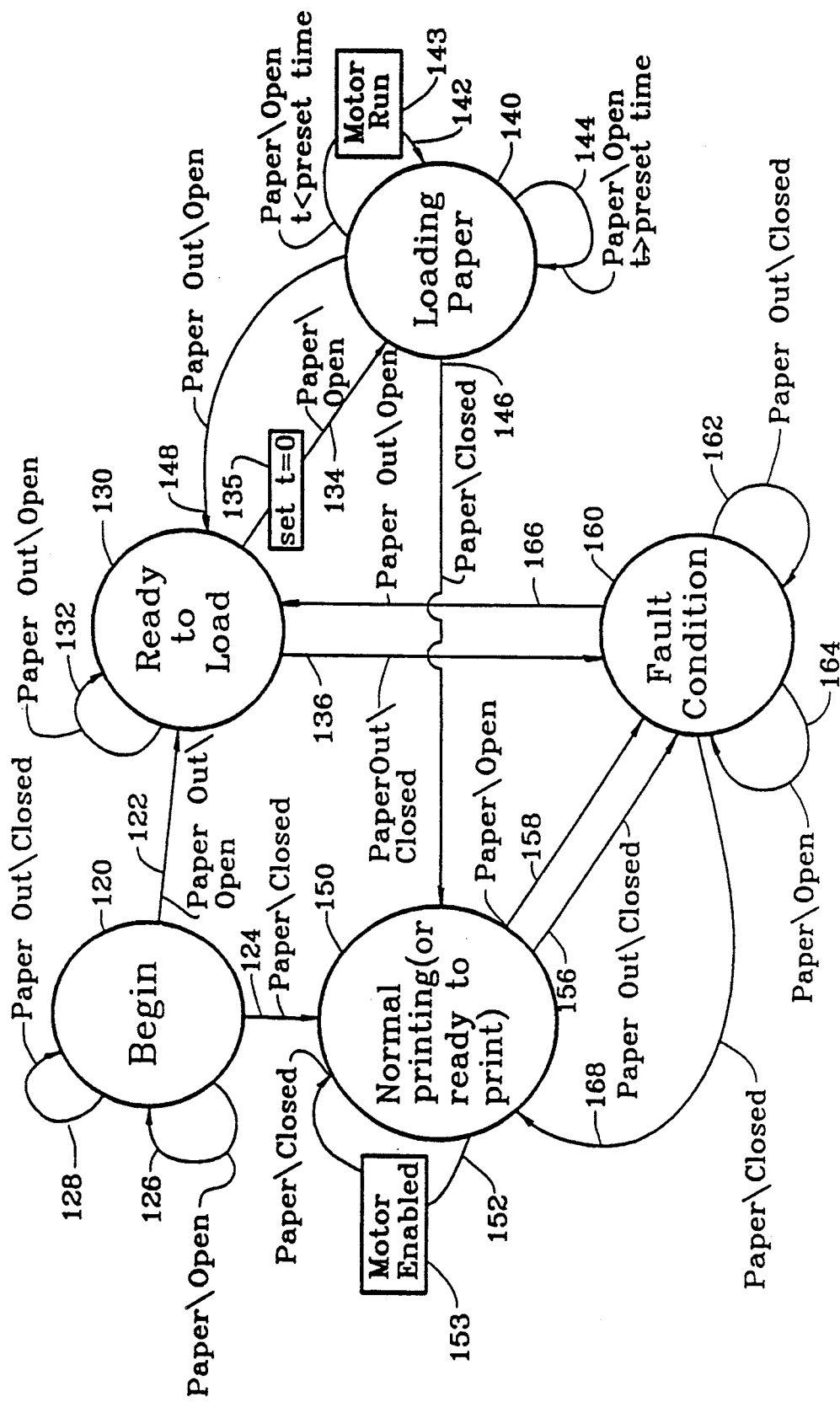
FIG. 12 is a state diagram of the paper feed state machine of the instant invention.

Both print head switch and paper out sensor 84 are connected to microprocessor 92 through the paper feed state machine module 98. Paper feed state machine module 98 is a software module which determines the state of the chart recorder 10 in order to initiate the "load sequence" and to operate in the Normal Printing state as described above. The state diagram for the paper state machine module 98 is shown in FIG. 12.

State machine consists of states 120, 130, 140, 150, and 160 which represent logical conditions. The logical conditions are dependent upon the condition of top of form sensor 76, print head switch 82 and paper out sensor 84, all of which are connected to microprocessor 92 which implements paper feed state machine module 98. When the condition of one of these external sensors or switches changes, the state machine moves from whatever state it is in to a different state as will be described hereafter. The source code for the paper state machine is contained in Appendix II.

The state diagram is entered through "Begin" state 120. "Begin" state 120 determines, when chart recorder 10 is turned on or reset, whether paper is present in chart recorder 10 and whether print head cover 46 is open or closed. If no paper is present and print head cover 46 is open, chart recorder 10 is ready to load the paper 2 through the chart recorder 10. In this case, the program passes along line 122 to "Ready to Load" state 130.

However, if paper is present and print head cover 46 is closed, chart recorder 10 is already loaded with paper and is ready to begin printing. Therefore, the program passes along line 124 to "Normal Printing" state 150 and bypasses the paper loading sequence of paper state feed machine 98.

If paper is present in chart recorder 10 but the print head cover 48 is open, there is no need to load paper into the recorder 10. However, the recorder 10 is not ready to begin printing since print head cover 46 is open. Consequently, the program passes through loop 126 from "Begin" state 120 back to "Begin" state 120 until the operator closes the print head cover 46. When the operator closes print head cover 46, chart recorder 10 is ready for printing and the program passes to "Normal Printing" state 150 along path 124 as described above.

While at "Begin" state 120, if no paper is present in chart recorder 10, but the print head cover 46 is closed, the chart recorder 10 is not ready to load paper or begin printing. As a result, the program passes through loop 128 from "Begin" state 120 back to "Begin" state 120 until the operator opens the print head cover 46. When print head cover 46 is opened, chart recorder 10 is ready to load paper so the program passes along path 122 to "Ready to Load" state 130 as described above.

At "Ready to Load" state 130, so long as the paper out sensor 84 indicates that there is no paper present at paper input 20 and the print head cover 46 is open, the program will continue to loop through loop 132 from "Ready to Load" state 130 back to "Ready to Load" state 130. In this condition, the chart recorder 10 is ready to load paper 2 as soon as paper 2 is presented to paper input 20.

At "Ready to Load" state 130 while the program is looping through loop 132 while waiting for paper 2 to be presented at paper input 20 so that the "loading" sequence can begin, if the operator closes print head cover 46, a "fault" condition is attained. The program then passes to "Fault Condition" state 160 along path 136.

At "Ready to Load" state 130, when paper 2 is presented at paper input 20 as indicated by paper out sensor 84, the program is ready to begin the "loading" sequence. This is done by the program passing from "Ready to Load" state 130 to "Loading Paper" state 140 along path 134. Along path 134, step 135 sets the time "t" to zero.

At "Loading Paper" state 140, so long as paper remains present in chart recorder 10, print head cover 46 remains open and the time "t" is less than the preset time for running motor 56 during the loading sequence as described above, the program passes through loop 142. In loop 142, motor 56 will run as shown in step 143, thereby passing paper 2 through chart recorder 10 as described in detail above.

When time "t" becomes equal to the preset time and thereafter, as long as the print head cover 46 remains open, the program loops through path 144 from "Loading Paper" state 140 back to "Loading Paper" state 140. This condition indicates that the paper 2 has been loaded but the print head cover has not been closed so printing can begin. When the operator closes the print head cover 46, the "loading" sequence is complete and the program passes to "Normal Printing" state 150 along path 146.

If, during the "loading" sequence while the program is looping through loop 142, paper out sensor 84 indicates that no paper 2 is present in paper input 20, this indicates that an insufficient amount of paper 2 was provided to properly load the chart recorder 10. In this case, the program passes from "Loading Paper" state 140 back to the "Ready to Load" state 130 along path 148. The program then proceeds as described above in connection with the description of the "Ready to Load" state 130.

At "Normal Printing" state 150, so long as paper is present in the chart recorder 10 as indicated by paper out sensor 84 and print head cover 46 is in the closed position as indicated by print head switch 82, "Normal Printing" state 150 allows printing on paper 2 by thermal print head 42 as directed by the larger control system of the ECG monitoring system or microprocessor 92 as desired. This condition is indicated by path 152 which loops from "Normal Printing" state 150 back to "Normal Printing" state 150. Step 153 indicates that motor 56 is enabled while passing through path 152 so that motor 56 may move paper 2 through the chart recorder 10 as directed by microprocessor 92.

If during the printing operation while at "Normal Printing" state 150, paper out sensor 84 indicates that paper 2 is no longer present in the chart recorder 10 while the print head cover 46 is in the closed position, a "fault" condition is present and the program passes from "Normal Printing" state 150 to "Fault Condition" state 160 along path 156.

If, during the printing operation at "Normal Printing" state 150, paper 2 is present and the operator opens the print head cover 46, a "fault" condition is indicated and the program passes from "Normal Printing" state 150 to "Fault Condition" state 160 through path 158.

"Fault Condition" state 160 is entered only when a "fault" condition is detected by paper state feed machine module 98. As described above, two "fault" conditions cause entry to "Fault Condition" state 160. The first "fault" condition is: no paper 2 indicated by paper out sensor 84 and print head cover 46 in the closed condition. This causes the program to move from either state 130 or 150 to "Fault Condition" state 160. The second "fault" condition can occur while in "Normal Printing" state 150. In this state, if paper 2 is present in chart recorder 10 as indicated by paper out sensor 84 and print head cover 46 is opened, a "fault" condition is attained and the program passes to "Fault Condition" state 160 along path 158.

While at "Fault Condition" state 160, as long as the "fault" condition exists, the program will loop through either path 162 or 164, depending on the "fault" condition, until some action is taken to correct the "fault" condition. Path 162 is the path the program takes if no paper 2 is indicated by paper out sensor 84 and print head cover 46 remains in a closed position. Path 164 is the path taken if paper 2 is present in the chart recorder 10 as indicated by paper out sensor 84 and print head cover 46 is in an open condition.

There are only two paths to leave "Fault Condition" state 160. First, if the program is looping through path 162 because no paper 2 is present in chart recorder 10 as indicated by paper out sensor 84 and the print head cover 46 is closed, upon the operator opening print head cover 46, the program moves from "Fault Condition" state 160 to "Ready to Load" state 130 along path 166. Once at "Ready to Load" state 130, the program waits by passing through loop 132 until paper 2 is presented at paper input 20 and detected by paper out sensor 84. Thereafter, the program passes from "Ready to Load" state 130 to "Loading Paper" state 140 as described above.

The second way to leave "Fault Condition" state 160 is when paper 2 is present within chart recorder 10 as indicated by paper out sensor 84 and print head cover 46 is open so that the program loops along path 164 from "Fault Condition" state 160 through loop 164 back to "Fault Condition" state 160. When the operator closes print head cover 46, the program passes from "Fault Condition" state 160 back to "Normal Printing" state 150 along path 168.

Host interface logic 100 is connected to microprocessor 92 in the preferred embodiment through host interface module 102. Host interface logic 100 is hardware which connects microprocessor 92 to the larger control system of an ECG monitoring device if such a larger control system is provided. Host interface module 102 is a software module which receives and reacts to commands from the larger control system to initiate corresponding responses in microprocessor 92. Host interface module 102 also sends information from microprocessor 92 back to the larger control system. When host interface logic 100 and host interface 102 are used in connection with the larger control system of an ECG monitoring device, the larger control system tells the chart recorder 10, among other things, when to start and stop, what speed to run at, the paper length being used, and where the "top of form" is located on the paper. In return, microprocessor 92 sends to the larger control system, through host interface logic 100 and host interface module 102, information about the status of chart recorder 10, warnings, self test results and the chart recorder's firmware identification number.

Speed module 104 is a software module which is connected to host interface module 102. In response to the direction from the larger control system through host interface module 102 for chart recorder 10 to run at a desired speed, speed module 104 passes a number selected from a chart stored in memory to step motor control logic module 106. The chart contains unique numbers corresponding to the desired speeds of operation. These stored numbers are processed by motor control logic module 106 and ultimately passed to timer 108. In response to step motor control logic module 106, timer 108 creates square wave pulses based on the retrieved stored number from the chart. The square wave pulses are passed to motor drive 110 through speed pulse line 112. The sequence of square waves passed to motor driver 110 determines the speed of rotation of motor 56 which in turn determines the speed that paper 2 is passed through the chart recorder 10. Speed module 104 and step motor control logic module 106, including timer 108, are software modules well known in the art in connection with such motors 56.

In addition to processing the stored number retrieved by speed module 104 and passing corresponding instructions to timer 108, step motor control logic 106 controls the operation of motor driver 110. Step motor control logic 106 is connected to paper feed state machine module 98 which determines which state the chart recorder 10 is in as described above. When paper feed state machine module 98 determines that the chart recorder 10 is in a state where the motor 56 may run, step motor control logic module 106 directs motor drive 110 to drive motor 56 according to the correct speed and length of time for the corresponding state.

Motor enable line 114 connects microprocessor 92 to motor drive 110. Step motor control logic 106 turns on and off motor driver 110 through motor enable line 114. Line 116 connects microprocessor 92 to motor driver 110. Step motor control logic 106 directs motor driver 110 through line 116 to advance the phases of the two step stepping motor 56 thereby enabling motor 56 to run.

Motor driver 110 is a switching transconductance amplifier such as is well known in the art. Motor driver 110 has two parts: a power controller and a H-bridge power driver, both of which are common in the art. Exemplary of a power controller is that made by the IXYS Company as the IXMS 150 power controller. Exemplary of the H-bridge power driver is that made by the SGS Company as Model L-298.

A reset line 118 is connected to both microprocessor 92 and motor drive 110. Reset line 118 sends a reset signal from the larger control system to microprocessor 92 and motor driver 110.

Although a microprocessor 92 has been described as controlling the electronic operations of the chart recorder 10, the microprocessor 92 could be replaced by a higher level data processor or by electronic hardware, both of which are familiar to those skilled in the art. Further, although the chart recorder 10 has been described as being controlled by the larger control system of an ECG monitoring device, chart recorder 10 could operate solely under the direction of microprocessor 92 with a connection to appropriate control interface hardware. In this embodiment, of course, the host interface logic 100 and host interface module 102 would not be needed. In addition, although the various aspects and elements of the chart recorder 10 described herein are intended to be integrated in use in a recorder 10, each element may be used either individually or in varying combinations as desired.

In addition, the instant invention has been described in connection with an ECG system. However, the chart recorder described herein may be used for recording any type of electrical signal.

While the instant invention has been described in connection with a specific embodiment, it is to be understood that the specific details of the description have been given by means of example only and not for limitation. It is clear that changes and modifications may be made to the description contained herein and still be within the scope of the claims. Further, obvious changes and modifications will occur to those skilled in the art.

APPENDIX I

```
/*===============================================================
.. !NAME!
    _Description

.. !1!

.. !include!="drv3:\q45\config\updc.inc"
```

370 Chart Recorder Automatic Paper Feed Module

Written by: John Rotunda
©1991 Quinton Instrument Co. All rights reserved.

Description:
  Performs Automatic Paper Feeding background task when enabled.
  This module works in the following way:
    - Detects State 1 (fault) based on a PO "out" state
    - Detects State 2 (ready to load) based on a HO "open" state
    - Runs State 3 (loading); runs paper motion speed at 50 mm/sec
    - Detects State 0 (normal) based on a HO "closed" state and no paper motion

| Functions Contained In AUTOFEED.C | Description Of Function: |
|---|---|

Primary Function:
   apf()                                         Controls the automatic paper feed function Function Tree Structure:

```
Called From MAIN.C Background
    |
    |____>  apf()
```

```
==========================================
==*/
/*
*/

/*----------------------------------------------------
   Includes:
-------------------------------------------------*/ include <GLOBLDEF.h>

/* allocate space for variables in following includes: */
#undef  GLOBAL
#define GLOBAL
#include "external.h"
#include "prifreg.h"
/*----------------------------------------------------
.. !2!
   Shared Data:
-------------------------------------------------*/

/* !/F2!
   <description>
!2! */

/* !END! - description section */

/*
/*----------------------------------------------------
.. !NAME!
     apf()

.. !1!

Description:
     This function controls all Automatic Paper Feed system states
     (fault, ready, loading and normal) and all associated APF control
     tasks. The APF function works in the following way:

FUNCTION BEGIN:

IF( The Paper Is In The Process Of Loading )
       IF( The APF "Fault" System State Is True )
         IF( HO Sensor Indicates A Head Open Condition )
           Clear The APF "Fault" System State To False
           Set The APF "Ready" System State To True
           Set Page_2 Of The Recorder Drive Status For Active APF
```

```
            IF( The APF "Ready" System State Is False )
              IF( PO Sensor Indicates A Paper Out Condition )
                Clear Page_2 Of The Recorder Drive Status APF Function To Off
                Clear The APF "Normal" System State To False
                Set The APF "Fault" System State To True
                Disable The Odometer Function
                Clear The Odometer To Zero IF( The Recorder Driver Status APF Override State Is False )
              IF( The APF "Ready" System State Is True )
                IF( PO Sensor Indicates A Seeing Paper Condition )
                  CALL: Set_speed( To 50 mm/sec )
                  CALL: Start_motor()
                  Clear The APF "Ready" System State To False
                  Set The APF "Loading" System State To True
                  Clear The Tof_Mark_Counter To Zero
              ELSE
                IF( The APF "Loading" System State Is True )
                  IF( HO Sensor Indicates A Head Closed Condition )
                    CALL: Stop()
                    Clear The APF "Loading" System State To False
                    Set The APF "Normal" System State To True
                    Set Page_2 Of The Recorder Drive Status For APF Not Active ELSE
                  IF( Tof_Mark_Counter >= One TOF Paper Marks )
                    Enable The Odometer To Count IF( Tof_Mark_Counter >= Two TOF Paper Marks )
                  AND ( The Odometer Is > The Minimum Valid Page Length )
                    Clear The Tof_Mark_Counter To Zero
                    CALL: Stop()
                    Clear The APF "Loading" System State To False
                    Set The APF "Normal" System State To True
                    Clear The Odometer To Zero
                    Set Page_2 Of The Recorder Drive Status For APF Not Active ELSE
              Clear The APF "Fault" System State To False
              Clear The APF "Ready" System State To False IF( ( The APF "Loading" System State Is True )
                CALL: Stop()
                Clear The Odometer To Zero
                Clear The APF "Loading" System State To False

RETURN

Parameters:
      None

Return:
      None

.. !0!
------------------------------------------------------------!-0!-*/ apf()

/* !/F2! */
{
```

```
if( SYS_STATUS.flags.loading == FALSE ) {        /* Paper loading state check */
    if( SYS_STATUS.flags.fault == TRUE ) {        /* APF state change check */
        if( ( rcdr_drv_status[ PRINT_STATUS ] & HO_STATUS_ON ) == HO_STATUS_ON ) {    /* Fault
to          ready state change check */
            SYS_STATUS.flags.fault = FALSE;          /* Clear the "fault" state condition */
            SYS_STATUS.flags.ready = TRUE;           /* Assert the "ready" state condition */
            rcdr_drv_status[ WARNING_STATUS ] |= APF_FUNCTION_ON; /* Assert the APF warning rcdr
                drive status */
        }
    }
    if( SYS_STATUS.flags.ready == FALSE ) {       /* APF not ready state check */
        if( ( rcdr_drv_status[ PRINT_STATUS ] & PO_STATUS_ON ) == PO_STATUS_ON ) {
            rcdr_drv_status[ WARNING_STATUS ] &= APF_FUNCTION_OFF;  /* APF warning rcdr drive
status           is off */
            SYS_STATUS.flags.normal = FALSE;         /* Clear the "normal" state condition */
            SYS_STATUS.flags.fault = TRUE;           /* Assert the "fault" state condition */
            MOTION_CONT.flags.enable_odometer = FALSE;   /* Disable the odometer function */
            MOTION_CONT.odometer = CLEAR;            /* Clear the odometer */
        }
    }
}
if( ( rcdr_drv_status[ OVERRIDE_STATUS ] & APF_OVERRIDE_ON ) == APF_OVERRIDE_ON
) {
    SYS_STATUS.flags.fault = FALSE;              /* Clear the "fault" state condition */
    SYS_STATUS.flags.ready = FALSE;              /* Assert the "ready" state condition */ if( SYS_STATUS.flags.loading == TRUE ) {     /* Paper "loading" check */
        stop();                                  /* Stop autofeeding process */
        SYS_STATUS.flags.loading = FALSE;        /* Clear the "loading" system state */
    }
    return;                                      /* Return on APF override */
}
if( SYS_STATUS.flags.ready == TRUE ) {           /* "Ready" system state check */
    if( ( rcdr_drv_status[ PRINT_STATUS ] & PO_STATUS_ON ) != PO_STATUS_ON ) {
        MOTION_CONT.real_speed = MM_SEC_50;      /* Save the real speed type */
        set_speed( MM_SEC_50 );                  /* Select 50 mm/sec paper speed */
        MOTION_CONT.flags.exe_free_run = TRUE;   /* Start the free-run sequence */
        SYS_STATUS.flags.ready = FALSE;          /* Clear the "ready" system state */
        SYS_STATUS.flags.loading = TRUE;         /* Assert the "loading" system state */
        SYS_STATUS.tof_mark_counter = CLEAR;     /* Clear the TOF mark counter for APF overrun
            condition */
    }
}
else {
    if( SYS_STATUS.flags.loading == TRUE ) {     /* Paper "loading" check */
        if( ( rcdr_drv_status[ PRINT_STATUS ] & HO_STATUS_ON ) != HO_STATUS_ON ) {    /* Halt
            autofeeding process check */
            stop();                              /* Stop autofeeding process */
            SYS_STATUS.flags.normal = TRUE;      /* Set the "normal" system state */
            MOTION_CONT.odometer = CLEAR;        /* Clear the odometer to zero */
            MOTION_CONT.flags.enable_odometer = TRUE;/* Enable the odometer function */
            rcdr_drv_status[ WARNING_STATUS ] &= APF_FUNCTION_OFF;  /* APF warning rcdr drive
status .         off */
        }
        else {
            if( SYS_STATUS.tof_mark_counter >= 1 )   /* First top of form marks */
                MOTION_CONT.flags.enable_odometer = TRUE;   /* Enable the odometer function */ if( SYS_STATUS.tof_mark_counter >= 2 ) { /* Second top of form marks */
                if( MOTION_CONT.odometer > APF_ODOMETER_LIMIT ) {
                    stop();                      /* Stop autofeeding process */
```

```
           SYS_STATUS.flags.normal = TRUE;        /* Set the "normal" system state */
           MOTION_CONT.flags.tof_check = FALSE;   /* At TOF, so reset the TOF checking flag */
           SYS_STATUS.tof_mark_counter = CLEAR;   /* Clear the TOF mark counter for APF function
                              */
           MOTION_CONT.odometer = CLEAR;          /* Clear the odometer to zero */
           rcdr_drv_status[ WARNING_STATUS ] &= APF_FUNCTION_OFF; /* Asert the APF warning
rcdr           drive status */
         }
         else                              /* Invalid TOF found */
           SYS_STATUS.tof_mark_counter = 1;       /* Set the TOF mark counter back to the provious
count          */
       }
      }
    }
   }
  }

/* !END!    END of function */
```

APPENDIX II

```
/*=================================================================
====
```

\_ !NAME!
  \_Description

\_ !!!

\_ !include! = "drv3:\q45\config\"updc.inc"

370 Chart Recorder Sensor Control Module

Written by: John Rotunda
©1991 Quinton Instrument Co. All rights reserved.

Description:
  This module performs all sensor checking and validation
  tasks. The 10mS Timer_1 interrupt calls the sensors() routine
  contained in this module which performs the followings tasks:

- Checks and validates the Top Of Form (TOF) sensor
  - Updates the odometer variable based on paper speed
  - Synchronizes odometer with TOF sensor if TOF sensor is good
  - Posts TOF sensor error status if TOF sensor fails
  - Keeps track of current paper position if TOF sensor fails
  - Checks, debounces and validates the Paper Out (PO) sensor
  - Checks, debounces and validates the Head Open (HO) sensor

| Functions Contained In SENSORS.C | Description Of Function: |
|---|---|
| Primary Function: | |
| sensors() | Performs all sensor control tasks |
| Support Functions: | |
| po_check() | Checks and validates paper out sensor |
| ho_check() | Checks and validates head open sensor |
| tof_check() | Checks and validates TOF sensor |

Top Down Design Of SENSORS.C

Function: sensors()
  - Controls PO, HO and TOF sensors by calling the following functions:
  Found In SENSORS.C Function: po_check()
      - Checks, debounces and validates the paper out sensor
      - Updates recorder driver Status
    Found In SENSORS.C Function: ho_check()
      - Checks, debounces and validates the head open sensor
      - Updates recorder driver Status
    Found In SENSORS.C Function: tof_check()
      - Checks for override status on TOF sensor
      - Checks, debounces and validates the top of form sensor
      - Updates recorder driver Status
      - Updates the odometer variable based on paper speed
      - Synchronizes odometer with TOF sensor if TOF sensor is good
    Found In SENSORS.C

```
==========================================================
===*/
/*
*/

/*----------------------------------------------------
    Includes:
-------------------------------------------------*/ include <GLOBLDEF.h>

/* allocate space for variables in following includes: */
#undef  GLOBAL
#define GLOBAL
#include "external.h"
#include "prifreg.h"

/*----------------------------------------------------
.. !2!
    Shared Data:
-------------------------------------------------*/

/* !/F2!
   <description>
!2! */

/* !END! - description section */

/*
/*----------------------------------------------------
.. !NAME!
    sensors()

.. !1!

Description:
    This function checks the PO, HO and TOF sensors by
``` calling three support functions. This routine is called by
the 10mS Timer_1 interrupt and works in the following way:

FUNCTION BEGIN:
  CALL: po_check()

CALL: ho_check()
  CALL: tof_check()
RETURN

Parameters:
  None

Return:
  None

.. !0!

----------------------------------------------------------!-0!-*/ sensors()

```
/* !/F2! */
{
  po_check();            /* Paper Out sensor check */
  ho_check();            /* Head Open sensor check */
  tof_check();           /* Top Of Form sensor check */
}
```

/* !END!  END of function */

/*
/*----------------------------------------------------------------
.. !NAME!
    po_check()

.. !1!

Description:
  This function checks, debounces and validates the
  paper out (PO) sensor. This function is called by sensors()
  and works in the following way:

FUNCTION BEGIN:

IF( PO Override State Is False )
    IF( PO Sensor Is Asserted )
      IF( PO Validation Counter >= Valid PO Count )
        Set rcdr_drv_status[ Page_0 ] To Paper Out Status
        CALL: stop()
      ELSE
        Increment The PO Validation Counter ELSE
      IF( PO Validation Counter Is Zero )
        Clear rcdr_drv_status[ Page_0 ] To Paper Loaded Status
      ELSE
        Decrement The PO Validation Counter

RETURN

Note: .

Valid PO Count Will Be Approximately Equal To Five.

Parameters:
    None

Return:
    None

.. !0!
———————————————————————————————!-0!-*/ po_check()

/* !/F2! */
{
  if( ( rcdr_drv_status[ OVERRIDE_STATUS ] & PO_OVERRIDE_ON ) != PO_OVERRIDE_ON ) {
    if( SPI.port_2.PO == ON_LOW ) {         /* PO sensor asserted check */
      if( MOTION_CONT.po_valid_counter >= VALID_PO ) {   /* PO multi-sample validation check */
        rcdr_drv_status[ PRINT_STATUS ] |= PO_STATUS_ON;   /* Set PO status to True */
        stop();                          /* Paper is out, stop paper motion */
      }
      else
        ++MOTION_CONT.po_valid_counter;     /* Continue to increment PO validation counter */
    }
    else {                                  /* HO non-asserted check */
      if( MOTION_CONT.po_valid_counter == 0 )
        rcdr_drv_status[ PRINT_STATUS ] &= PO_STATUS_OFF;  /* Clear the po rcdr driver status */
      else
        --MOTION_CONT.po_valid_counter;     /* Continue to decrement PO validation counter */
    }
  }
}

/* !END!   END of function */

/*
/*--------------------------------------------------------------
.. !NAME!
    ho_check()

.. !1!

Description:
    This function checks, debounces and validates the
    head open (HO) sensor. This function is called by sensors()
    and works in the following way:

FUNCTION BEGIN:

IF( HO Override State Is False )
    IF( HO Sensor Is Asserted )
      IF( HO Validation Counter >= Valid HO Count )
        Set rcdr_drv_status[ Page_0 ] To Head Open Status
      ELSE
  Increment The HO Validation Counter ELSE
  IF( HO Validation Counter Is Zero )
    Clear rcdr_drv_status[ Page_0 ] To Head Closed Status
  ELSE
    Decrement The HO Validation Counter

RETURN

Note:
Valid HO Count Will Be Approximately Equal To Five.

Parameters:
None

Return:
None

.. !0!
───────────────────────────────────────────────!-0!-*/ ho_check()

/* !/F2! */
{
  if( ( rcdr_drv_status[ OVERRIDE_STATUS ] & HO_OVERRIDE_ON ) != HO_OVERRIDE_ON ) {
    if( SPI.port_1.HEAD_OPEN == ON_LOW ) {     /* HO sensor asserted check */
      if( MOTION_CONT.ho_valid_counter >= VALID_HO )    /* HO multi-sample validation check
*/
        rcdr_drv_status[ PRINT_STATUS ] |= HO_STATUS_ON;   /* Set HO status to True */
      else
        ++MOTION_CONT.ho_valid_counter;         /* Continue to increment HO validation counter */
    }
    else {                          /* HO non-asserted check */
      if( MOTION_CONT.ho_valid_counter == 0 )
        rcdr_drv_status[ PRINT_STATUS ] &= HO_STATUS_OFF;  /* Clear the ho rcdr driver status */
      else
        --MOTION_CONT.ho_valid_counter;         /* Continue to decrement HO validation counter */
    }
  }
}

/* !END!   END of function */

/*
/*───────────────────────────────────────────────
.. !NAME!
    tof_check()

.. !1!

Description:
    This function checks, debounces and validates the
    top of form (TOF) sensor and updates the odometer variable
    based on paper speed. The odometer acts as the backup TOF sensor
    if the TOF sensor fails and if the TOF override state is asserted.
    This function is called by sensors() and works in the following way:

FUNCTION BEGIN:

IF( RUN Is Active And APF System State Is "Normal" )
        Increment The Odometer Based On Paper Speed IF( ( Paper Position Odometer > 40 mm )
            AND ( Paper Position Odometer < 285 mm ) )
            Set Check Next TOF State To True IF( Paper Position Odometer >= 285 mm )
            Set rcdr_drv_status[ Page_1 ] To TOF Sensor Error

```
        IF( TOF Override Status Is Asserted )
          Set rcdr_drv_status[ Page_0 ] TOF Status IF( Paper Position Odometer >= 290 mm )
          Reset The Odometer To 10 mm IF( TOF Override Status Is Asserted )
              Reset rcdr_drv_status[ Page_0 ] TOF Status IF( TOF Override Status Is Not Asserted )
        IF( TOF Sensor Is Asserted )
          IF( TOF Validation Counter >= Valid TOF Count )
            IF( rcdr_drv_status[ Page_0 ] Indicates TOF Has Just Been Found (False) )
              Increment Tof_Mark_Counter By One
              Set rcdr_drv_status[ Page_0 ] Top Of Form Status
              Reset The Paper Position Odometer To Zero
            ELSE
              Increment The TOF Validation Counter ELSE
          IF( TOF Validation Counter Is Zero )
            Clear rcdr_drv_status[ Page_0 ] Top Of Form Status
          ELSE
            Decrement The TOF Validation Counter

RETURN

Note:
        Valid TOF Count Will Be Approximately Equal To three.

Parameters:
        None

Return:
        None

.. !0!
------------------------------------------------------------!-0!-*/ tof_check()

/* !/F2! */
{
  if( ( rcdr_drv_status[ OVERRIDE_STATUS ] & TOF_OVERRIDE_ON ) == TOF_OVERRIDE_ON
)                /* Enable odometer if TOF override is ON */
    MOTION_CONT.flags.enable_odometer = TRUE;           /* Enable the odometer function */ if( ( SCI.port1.RUN == ON_LOW ) && ( MOTION_CONT.flags.enable_odometer == TRUE ) ) { /*
            Motor running check */
    if( ++MOTION_CONT.flags.inc_odometer == TRUE )           /* Increment odometer check */
       MOTION_CONT.odometer += 5*MOTION_CONT.real_speed;     /* Increment odometer based
on          paper speed */ if( SYS_STATUS.flags.loading == FALSE ) {
      if( ( rcdr_drv_status[ OVERRIDE_STATUS ] & TOF_OVERRIDE_ON ) != TOF_OVERRIDE_ON
)               { /* TOF override check for end of TOF mark */
        if( ( MOTION_CONT.odometer >= 4000 )
          && ( MOTION_CONT.odometer < ODOMETER_TOF_LIMIT ))   /* TOF valid check at after
              paper mark is detected */
          MOTION_CONT.flags.tof_check = TRUE;           /* TOF check is valid now */ if( MOTION_CONT.odometer >= ODOMETER_TOF_LIMIT )      /* Odometer TOF sensor
max           limit check */
```

```
                    rcdr_drv_status[ ERROR_STATUS ] |= TOF_SENSOR_FAIL;   /* Set TOF sensor failure status
to                  True */
                }
                else {                                       /* TOF override is true check */
                    if( ( MOTION_CONT.odometer >= 4000 )
                     && ( MOTION_CONT.odometer < MOTION_CONT.paper_length ) ) { /* TOF valid check at
after               paper mark is detected */
                        MOTION_CONT.flags.tof_check = TRUE;          /* TOF check is valid now */
                        rcdr_drv_status[ ERROR_STATUS ] &= TOF_SENSOR_OK;   /* Clear TOF sensor failure
status              */
                    }
                    if( MOTION_CONT.odometer >= MOTION_CONT.paper_length ) {  /* Odometer TOF sensor
max                 limit check */
                        rcdr_drv_status[ PRINT_STATUS ] |= TOF_STATUS_ON;    /* Set TOF status to True */ if( MOTION_CONT.odometer >= MOTION_CONT.paper_length+TOF_MARK_LENGTH ) {
/*                      Odometer TOF sensor end mark check */
                            MOTION_CONT.odometer = TOF_MARK_LENGTH;           /* Preset the paper motion
                                odometer to the TOF mark length */
                            MOTION_CONT.flags.inc_odometer = TRUE;            /* Re-initialize the odometer */
                            rcdr_drv_status[ PRINT_STATUS ] &= TOF_STATUS_OFF;  /* Set TOF status to True */
                        }
                    }
                }
            }
        }
        if( ( rcdr_drv_status[ OVERRIDE_STATUS ] & TOF_OVERRIDE_ON ) != TOF_OVERRIDE_ON )
        {
            if( SPI.port_2.TOF == ON_LOW ) {            /* TOF sensor asserted check */
                if( MOTION_CONT.tof_valid_counter >= VALID_TOF ) {   /* TOF multi-sample validation check
*/
                    if( ( rcdr_drv_status[ PRINT_STATUS ] & TOF_STATUS_ON ) != TOF_STATUS_ON )
                        ++SYS_STATUS.tof_mark_counter;           /* Increment the TOF mark counter for APF
                            function */ rcdr_drv_status[ PRINT_STATUS ] |= TOF_STATUS_ON;    /* Set TOF status to True */
                    rcdr_drv_status[ ERROR_STATUS ] &= TOF_SENSOR_OK;    /* Set TOF sensor failure status
to                  True */ if( SYS_STATUS.flags.loading == FALSE )
                        MOTION_CONT.odometer = 0;         /* Clear the paper motion odometer */
                }
                else
                    ++MOTION_CONT.tof_valid_counter;      /* Continue to increment TOF validation counter */
            }
            else {                                     /* TOF non-asserted check */
                if( MOTION_CONT.tof_valid_counter == 0 )
                    rcdr_drv_status[ PRINT_STATUS ] &= TOF_STATUS_OFF;    /* Clear the tof rcdr driver status
*/
                else
                    --MOTION_CONT.tof_valid_counter;      /* Continue to decrement TOF validation counter */
            }
        }
    }
}

/* !END!   END of function */
```

What is claimed is:

1. In a printing device having a print head for inscribing paper positioned in proximity to the print head, the print head movable into and out of a position to inscribe the positioned paper, a system for loading and aligning the paper in the device by moving paper in a direction along a paper path through the device comprising:
   a) means for receiving the paper to be loaded into the printing device;
   b) means, located along the paper path before said means for receiving the paper to be loaded, for detecting the presence of paper at said means for receiving the paper;

c) means for detecting when the print head is out of position to inscribe the paper; and, d) means, responsive to both an indication by said means for detecting the presence of paper that paper is present at said means for receiving the paper and an indication by said means for detecting when the print head is out of position that the print head is out of position to inscribe the paper, for moving paper presented at said means for receiving the paper through the printing device into a position to be inscribed by the print head when the print head is thereafter moved into a position to inscribe the paper.

2. The system of claim 1 wherein said means for moving paper moves the paper through the printing device for a predetermined time period.

3. The system of claim 1 further comprising means for determining when the paper is located at a top of form position and wherein said means for moving paper moves the paper through the printing device until said means for determining when the paper is located at the top of form position determines that the paper is located at the top of form position.

4. The loading system of claim 1 further comprising an inner and an opposed outer guide surface located within the printing device, between which the paper to be inscribed by the print head passes through the printing device, said inner and outer guide surfaces positioning the paper at the print head.

5. The loading system of claim 1 further comprising an elongated print roller for supporting the paper in contact with the print head, the print roller disposed parallel to the print head, a longitudinal axis of said print roller located transverse to a direction of paper movement along the paper path.

6. The loading system of claim 1 wherein said means for moving paper comprises:

a) a cylindrical feed roller located along the paper path after said means for receiving the paper, a longitudinal axis of said feed roller located transverse to the direction of the paper movement along the paper path;

b) means for allowing said feed roller to rotate about said feed roller longitudinal axis; and, c) means for rotating said feed roller about said feed roller longitudinal axis whereby frictional contact between said feed roller and the paper moves the paper past said feed roller and through the printing device as said feed roller rotates.

7. The loading system of claim 6 further comprising means for holding the paper in contact with said feed roller.

8. The loading system of claim 7 wherein said means for holding the paper in contact with said feed roller comprises a snub roller having a longitudinal axis parallel to the longitudinal axis of said feed roller, the longitudinal axis of said snub roller located transverse to the direction of the paper movement along the paper path, said snub roller having means for allowing said snub roller to rotate about said snub roller longitudinal axis, said snub roller adapted to interact with said feed roller so that rotation of said feed roller causes said snub roller to rotate.

9. The system of claim 6 wherein said means for rotating said feed roller comprises a motor having a rotating member and means for connecting said rotating member to said feed roller.

10. The system of claim 9 wherein said means for connecting said rotating member to said feed roller comprises:

a) a feed roller pulley attached to one end of said feed roller, a central axis of said feed roller pulley being collinear with the longitudinal axis of said feed roller; and, b) means for transferring the rotation of said rotating member to said feed roller pulley so that rotation of said rotating member causes said feed roller pulley to rotate.

11. The loading system of claim 1 further comprising:

a) an inner and an opposed outer guide surface located within the printing device, between which the paper to be inscribed by the print head passes through the printing device, said inner and outer guide surfaces positioning the paper at the print head;

b) a print roller for supporting the paper in contact with the print head, the print roller disposed parallel to the print head, a longitudinal axis of said print roller located transverse to a direction of paper movement along the paper path; and, wherein said means for moving paper comprises:

a) a cylindrical feed roller located along, the paper path after said means for receiving the paper, a longitudinal axis of said feed roller located transverse to the direction of the paper movement along the paper path;

b) means for allowing said feed roller to rotate about said feed roller longitudinal axis;

c) means for holding the paper in contact with said feed roller;

d) means for rotating said feed roller about said feed roller longitudinal axis whereby frictional contact between said feed roller and the paper moves the paper past said feed roller and through the printing device as said feed roller rotates; and, e) means, attached to said means for detecting the presence of paper and said means for detecting when the print head is moved, for controlling said means for rotating said feed roller so that when said means for detecting the presence of paper indicates the presence of paper and said means for detecting when the print head is out of position to inscribe the paper, said, means for, controlling said means for rotating said feed roller directs said means for rotating to rotate for a predetermined time so that the paper is passed between said feed roller and said means for holding the paper in contact with said feed roller by contact of the paper with the rotating feed roller and corresponding means for holding the paper in contact with said feed roller, and whereafter, the paper is passed between said inner and outer guide surfaces where the paper is directed between the print head and said print roller, and whereafter, after the predetermined time has elapsed, said means for rotating ceases to rotate thereby positioning the paper between the print head and said print roller so that the print head may be moved into a position to inscribe the paper by moving the print head into contact with the paper upon said print roller.

12. The loading system of claim 1 further comprising:
a) an inner and an opposed outer guide surface located within the printing device, between which the paper to be inscribed by the print head passes through the printing device, said inner and outer guide surfaces positioning the paper at the print head;
b) a print roller for supporting the paper in contact with the print head, the print roller disposed parallel to the print head, a longitudinal axis of said print roller located transverse to the direction of paper movement along the paper path; and,
wherein said means for moving paper comprises:
a) a cylindrical feed roller located along the paper path after said means for receiving the paper, the longitudinal axis of said feed roller located transverse to the direction of paper movement along the paper path;
b) means for allowing said feed roller to rotate about said feed roller longitudinal axis;
c) means for holding the paper in contact with said feed roller;
d) means for rotating said feed roller about said feed roller longitudinal axis whereby frictional contact between said feed roller and the paper moves the paper past said feed roller and through the printing device as said feed roller rotates;
e) means for determining when the paper is located at a top of form position; and,
f) means, attached to said means for detecting the presence of paper and said means for detecting when the print head is moved, for controlling said means for rotating said feed roller so that when said means for detecting the presence of paper indicates the presence of paper and said means for detecting when the print head is out of position to inscribe the paper, said means for controlling said means for rotating said feed roller directs said means for rotating to rotate until said means for determining when the paper is located at the top of form position determines that the paper is located at the top of form position so that the paper is passed between said feed roller and said means for holding the paper in contact with said feed roller by contact of the paper with the rotating feed roller and corresponding means for holding the paper in contact with said feed roller, and whereafter, the paper is passed between said inner and outer guide surfaces where the paper is directed between the print head and said print roller and whereafter, after said means for determining when the paper is located at the top of form position determines that the paper is located at the top of form position, said means for rotating ceases to rotate thereby positioning the paper between the print head and said print roller so that the print head may be moved into a position to inscribe the paper by moving the print head into contact with the paper upon said print roller.

13. The loading system of claim 1 wherein said means for detecting the presence of paper comprises an electromagnetic wave emitter and an opposed corresponding detector, said emitter and detector adapted to allow the paper to pass therebetween so that when paper is present between said emitter and said detector, the electromagnetic wave from said emitter is blocked by the paper and therefore not detected by said detector.

14. The loading system of claim 1 wherein said means for detecting when the print head is out of position comprises a switch actuated by the movement of the print head into and out of position to inscribe the paper.

15. The loading system of claim 1 further comprising a control system, connected to both said means for detecting the presence of paper and said means for detecting when the print head is out of position to inscribe the paper, for directing said means for moving paper to move paper through the printing device.

16. The loading system of claim 15 wherein said control system includes a microprocessor for directing said control system.

17. The system of claim 1 further comprising:
a) an inner and an opposed outer guide surface located within the printing device, between which the paper to be inscribed by the print head passes through the printing device, said inner and outer guide surfaces positioning the paper at the print head;
b) a cylindrical feed roller located along the paper path before the inner guide surface, said feed roller having means for allowing said feed roller to rotate about a longitudinal axis of said feed roller, the longitudinal axis of feed roller located transverse to a direction of paper movement along the paper path, said feed roller having a surface in frictional contact with the paper;
c) means, located along the paper path after said inner guide surface, for moving paper through the printing device after the paper has been loaded into the printing device;
d) means for rotating said feed roller at a rotational rate so that an outer circumferential surface of said feed roller, while being rotated by said means for rotating said feed roller, moves at a slower speed than the paper is moved through the printing device by said means for moving paper through the printing device; and,
e) means for allowing said feed roller to rotate at a faster rate than said feed roller is being rotated by said means for rotating said feed roller whereby the paper, when loaded into the printing device, contacts both said feed roller and said means for moving paper and said means for moving paper imparts movement to the paper, and whereby dissipative resistance forces in said means for allowing said feed roller to rotate about said feed roller longitudinal axis and said means for allowing said feed roller to rotate at a faster rate causes said feed roller to resist being rotated by frictional contact with the moving paper thereby imparting drag to the paper through frictional contact between said feed roller and the paper thereby causing tension in the paper between said feed roller and said means for moving paper which tension moves the paper into contact with the inner guide surface for precisely positioning the paper for printing by the print head.

18. The system of claim 1 further comprising:
a) an inner guide surface for contacting paper to be inscribed by the printing device;
b) a cylindrical feed roller located along the paper path before the inner guide surface, said feed roller having means for allowing said feed roller to rotate about a longitudinal axis of said feed roller, the longitudinal axis of said feed roller located transverse to a direction of paper movement along the paper path, said feed roller having a surface in frictional contact with the paper;

c) means, located along the paper path after the inner guide surface, for moving paper through the printing device;

d) means for rotating said feed roller at a rotational rate so that an outer circumferential surface of said feed roller, while being rotated by said means for rotating said feed roller, moves at a slower speed than the paper is moved through the printing device by said means for moving paper through and printing device; and, e) means for allowing said feed roller to rotate at a faster rate than said feed roller is being rotated by said means for rotating said feed roller whereby the paper, when loaded into the printing device, contacts both said feed roller and said means for moving paper, and said means for moving paper imparts movement to the paper, and whereby dissipative resistance forces in said means for allowing said feed roller to rotate about said feed roller longitudinal axis and said means for allowing said feed roller to rotate at a faster rate causes said feed roller to resist being rotated by frictional contact with the moving paper thereby imparting drag to the paper through frictional contact between said feed roller and the paper thereby causing tension in the paper between said feed roller and said means for moving paper which tension moves the paper into contact with the inner guide surface for precisely positioning the paper for printing by the print head.

19. The system of claim 18 wherein said means for allowing said feed roller to rotate at a faster rate comprises a one-way clutch.

20. The system of claim 1 further comprising:
a) means for moving paper through the printing device at a constant speed;
b) means for measuring a length of time said means for moving paper has moved paper through the device; and
c) means for multiplying the length of time said means for moving paper has moved paper through the device by a rate that said means for moving paper has moved paper through the device.

21. The system of claim 20 further comprising means for calculating when the length of paper moved through the printing device equals a predetermined length and for producing a control signal in response thereto.

22. The system of claim 21 further comprising means responsive to said control signal for causing said means for moving paper to cease moving paper thereby positioning the paper at a "top of form" position.

23. The system of claim 1 further comprising:
a) means for positioning paper, to be inscribed by the printing device, in proximity to the print head;
b) a cylindrical feed roller located along the paper path before said means for positioning paper, said feed roller having means for allowing said feed roller to rotate about a longitudinal axis of said feed roller, the longitudinal axis of said feed roller located transverse to a direction of paper movement along the paper path, said feed roller having a surface in frictional contact with the paper;
c) means, located along the paper path after said means for positioning paper, for moving paper through the printing device;

d) means for rotating said feed roller at a rotational rate so that an outer circumferential surface of said feed roller, while being rotated by said means for rotating said feed roller, moves at a slower speed than the paper is moved through the printing device by said means for moving paper through the printing device; and, e) means for allowing said feed roller to rotate at a faster rate than said feed roller is being rotated by said means for rotating said feed roller whereby the paper, when loaded into the printing device, contacts both said feed roller and said means for moving paper and said means for moving paper imparts movement to the paper, and whereby dissipative resistance forces in said means for allowing said feed roller to rotate about said feed roller longitudinal axis and said means for allowing said feed roller to rotate at a faster rate causes said feed roller to resist being rotated by frictional contact with the moving paper thereby imparting drag to the paper through frictional contact between said feed roller and the paper thereby causing tension in the paper between said feed roller and said means for moving paper which tension moves the paper into contact with said means for positioning paper for printing by the print head.

24. In a printing device having an inner guide surface for contacting paper to be inscribed by the printing device, the printing device also having a print head movable into contact with the paper, the printing device also having a means for receiving paper to the printing device located along a paper path before the inner guide surface, a system for precisely positioning the paper with respect to the print head comprising:

a) a cylindrical feed roller located along the paper path before the inner guide surface, said feed roller having means for allowing said feed roller to rotate about a longitudinal axis of said feed roller, the longitudinal axis of said feed roller located transverse to a direction of paper movement along the paper path, said feed roller having a surface in frictional contact with the paper;

b) means, located along the paper path after the inner guide surface, for moving paper through the printing device;

c) means for rotating said feed roller at a rotational rate so that the outer circumferential surface of said feed roller, while being rotated by said means for rotating said feed roller, moves at a slower speed than the paper is moved through the printing device by said means for moving paper through the printing device; and, d) means for allowing said feed roller to rotate at a faster rate than said feed roller is being rotated by said means for rotating said feed roller whereby the paper, when loaded into the printing device, contacts both said feed roller and said means for moving paper and said means for moving paper imparts movement to the paper, and whereby dissipative resistance forces in said for allowing said feed roller to rotate axis about said feed roller longitudinal axis and said means for allowing said feed roller to rotate at a faster rate causes said feed roller to resist being rotated by frictional contact with the moving paper thereby imparting drag to the paper through frictional contact between said feed roller and the paper thereby causing tension in the paper between said feed roller and said means for moving paper which tension moves the paper into contact with the inner guide surface for precisely positioning the paper for printing by the print head.

25. The system of claim 24 wherein said means for moving paper comprises:
   a) a cylindrical print roller having a longitudinal axis parallel to the print head and transverse to the direction of the paper movement along the paper path, said print roller having means for allowing said print roller to rotate about said print roller longitudinal axis; and,
   b) means for rotating said print roller about said print roller longitudinal axis,
   whereby frictional contact between the paper and said print roller as said print roller rotates moves the paper through the printing device.

26. The system of claim 24 further comprising:
   a) means for moving paper through the printing device at a constant speed;
   b) means for measuring a length of time the means for moving paper has moved paper through the device; and,
   c) means for multiplying the length of time the means for moving paper has moved paper through the device by a rate that the means for moving paper moves paper through the device.

27. The system of claim 24, wherein said means for allowing said feed roller to rotate at a faster rate comprises a one-way clutch.

28. In a printing device, having a means for moving paper through the printing device at a constant speed to produce a rate of paper movement through the printing device, a system for determining the amount of paper passed through the printing device comprising:
   a) means for measuring a length of time the means for moving paper has moved paper through the device comprising a microprocessor connected to the means for moving paper, said microprocessor having a volatile memory means and a timer means, said timer means timing the length of time the means for moving paper has moved paper through the device and storing a representative value of the length of time in said memory means;
   b) means, implemented on said microprocessor, for multiplying said representative value of the length of time the means for moving paper has moved paper through the device, stored in said memory means, by a rate that the means for moving paper moves paper through the device to produce a value representative of the length of paper moved through the device; and,
   c) means, responsive to said value representative of the length of paper moved through the device, for controlling the means for moving paper through the printing device.

29. The system of claim 28 further comprising means, implemented on said microprocessor, for calculating when the length of paper moved through the printing device equals a predetermined length and for producing a control signal in response thereto.

30. The system of claim 29 further comprising means responsive to said control signal for causing said means for moving paper to cease moving paper thereby positioning the paper at a "top of form" position.

31. The system of claim 28 wherein said timer means includes: means implemented on said microprocessor, for incrementing at a first desired time interval, a value stored in said memory means representative of a second desired time interval where said second desired time interval is larger than said first desired time interval.

32. In a printing device having a means for moving paper along a paper path through the printing device at a constant speed, the means for moving operating in response to a control signal, a system for preventing excess paper beyond a predetermined length from being moved through the printing device comprising:
   a) means for measuring a length of time the means for moving paper has moved paper through the device;
   b) means for multiplying the measured length of time the means for moving paper has moved paper through the device a rate that the means for moving paper moves paper through the device;
   c) means for calculating when a length of paper moved through the printing device equals a predetermined length; and,
   d) means for producing a control signal for controlling the operation of the means for moving paper, said control signal produced in a first state in response to a calculation by said means for calculating that the length of paper moved through the printing device equals a predetermined length and said control signal produced in a second state in response to a calculation by said means for calculating that the length of paper moved through the printing device does not equal a predetermined length.

33. The system of claim 32 wherein the means for moving, in response to said control signal produced in said first state, causes the means for moving paper to cease moving paper.

34. In a printing device having a means for moving paper along a paper path through the printing device at a constant speed, a system for positioning the paper at a top of form position comprising:
   a) means for measuring a length of time the means for moving paper has moved paper through the device;
   b) means for multiplying the length of time the means for moving paper has moved paper through the device by a rate that the means for moving paper moves paper through the device;
   c) means for calculating when the length of paper passed through the printing device equals a predetermined length and for producing a control signal in response thereto; and,
   d) means, responsive to said control signal, for causing said means for moving paper to cease moving paper thereby positioning the paper at the top of form position.

35. A printing device comprising:
   a) a print head for inscribing paper positioned in proximity to the print head, the print head movable into and out of a position to inscribe the positioned paper;
   b) an inner guide surface for contacting paper to be inscribed by said print head;
   c) means for receiving paper to the printing device located along a paper path before said inner guide surface;
   d) means for moving paper along the paper path through the printing device at a constant speed;
   e) means for detecting the presence of paper at said means for receiving paper;
   f) means for detecting when said print head is out of position to inscribe the paper;

g) means, responsive to both an indication by said means for detecting the presence of paper that paper is present at said means for receiving paper and an indication by said means for detecting when the print head is out of position that the print head is out of position to inscribe the paper, for moving paper presented at said means for receiving paper through the printing device into a position to be inscribed by said print head when said print head is thereafter moved into a position to inscribe the paper;

h) a cylindrical feed roller located along the paper path before said inner guide surface, said feed roller having means for allowing said feed roller to rotate about a longitudinal axis of said feed roller, the longitudinal axis of said feed roller located transverse to a direction of paper movement along the paper path, said feed roller having a surface in frictional contact with the paper;

i) means, located along the paper path after said inner guide surface, for moving paper through a printing device;

j) means for rotating said feed roller at a rotational rate so that the outer circumferential surface of said feed roller, while being rotated by said means for rotating said feed roller, moves at a slower speed than the paper is moved through the printing device by said means for moving paper through the printing device;

k) means for allowing said feed roller to rotate at a faster rate than said feed roller is being rotated by said means for rotating said feed roller whereby the paper, when loaded into the printing device, contacts both said feed roller and said means for moving paper and said means for moving paper imparts movement to the paper, and whereby dissipative resistance forces in said means for allowing said feed roller to rotate about said feed roller's longitudinal axis and said means for allowing said feed roller to rotate at a faster rate cause said feed roller to resist being rotated by frictional contact with the moving paper thereby imparting drag to the paper through frictional contact between said feed roller and the paper thereby causing tension in the paper between said feed roller and said means for moving paper which tension moves the paper into contact with said inner guide surface for precisely positioning the paper for printing by said print head;

l) means for measuring a length of time the means for moving paper has moved paper through the device;

m) means for multiplying the length of time said means for moving paper has moved through the device by a rate that said means for moving paper moves paper through the device;

n) means for calculating when the length of paper passed through the printing device equals a predetermined length and for producing a control signal in response thereto; and, o) means, responsive to said control signal, for causing said means for moving paper to cease moving paper thereby positioning the paper at a "top of form" position.

36. In a printing device having a print head for inscribing paper positioned in proximity to the print head, the print head movable into and out of a position to inscribe the positioned paper, a combination system for loading and aligning paper in the device by moving the paper along a paper path through the device and for precisely positioning the paper with respect to the print head comprising:

a) means for receiving the paper to be loaded into the printing device;

b) means for detecting the presence of paper at said means for receiving the paper;

c) means for detecting when the print head is out of position to inscribe the paper;

d) means, responsive to both an indication by said means for detecting the presence of paper that paper is present at said means for receiving the paper and an indication by said means for detecting when the print head is out of position that the print head is out of position to inscribe the paper, for moving paper presented at said means for receiving the paper through the printing device into a position to be inscribed by the print head when the print head is thereafter moved into a position to inscribe the paper;

e) means for positioning paper, to be inscribed by the printing device, in proximity to the print head;

f) a cylindrical feed roller located along the paper path before said means for positioning paper, said feed roller having means for allowing said feed roller to rotate about a longitudinal axis of said feed roller, the longitudinal axis of said feed roller located transverse to a direction of paper movement along the paper path, said feed roller having a surface in frictional contact with the paper;

g) means, located along the paper path after said means for positioning paper, for moving through the printing device along the paper path;

h) means for rotating said feed roller at a rotational rate so that an outer circumferential surface of said feed roller, while being rotated by said means for rotating said feed roller, moves at a slower speed than the paper is moved through the printing device by said means for moving paper through the printing device; and, i) means for allowing said feed roller to rotate at a faster rate than said feed roller is being rotated by said means for rotating said feed roller whereby the paper, when loaded into the printing device, contacts both said feed roller and said means for moving paper and said means for moving paper imparts movement to the paper, and whereby dissipative resistive forces in said means for allowing said feed roller to rotate about said feed roller's longitudinal axis and said means for allowing said feed roller to rotate at a faster rate causes said feed roller to resist being rotated by frictional contact with the moving paper thereby imparting drag to the paper through frictional contact between said feed roller and the paper thereby causing tension in the paper between said feed roller and said means for moving paper which tension moves the paper into contact with said means for positioning paper for precisely positioning the paper for printing by the print head.

37. In a paper printing device having a print head movable into contact with the paper, the printing device also having a means for positioning paper to be inscribed by the printing device in proximity to the print head along a print path, the printing device also having a means for receiving paper to the printing device located along the paper path before the means for positioning paper, a system for precisely positioning the paper with respect to the print head comprising:

a) a cylindrical feed roller located along the paper path before the means for positioning, said feed roller having means for allowing said feed roller to rotate about a longitudinal axis of said feed roller, the longitudinal axis of said feed roller located transverse to a direction of paper movement along the paper path, said feed roller having a surface in frictional contact with the paper;

b) means, located along the paper path after the means for positioning, for moving paper through the printing device;

c) means for rotating said feed roller at a rotational rate so that an outer circumferential surface of said feed roller, while being rotated by said means for rotating said feed roller, moves at a slower speed than the paper is moved through the printing device by said means for moving paper through the printing device; and, d) means for allowing said feed roller to rotate at a faster rate than said feed roller is being rotated by said means for rotating said feed roller whereby the paper, when loaded into the printing device, contacts both said feed roller and said means for moving paper and said means for moving paper imparts movement to the paper, and whereby dissipative resistance forces in said means for allowing said feed roller to rotate about said feed roller longitudinal axis and said means for allowing said feed roller to rotate at a faster rate causes said feed roller to resist being rotated by frictional contact with the moving paper thereby imparting drag to the paper through frictional contact between said feed roller and the paper thereby causing tension in the paper between said feed roller and said means for moving paper which tension moves the paper into contact with the means for positioning for precisely positioning the paper for printing by said print head.

38. In a printing device having means for moving paper through the printing device at a constant speed to produce a rate of paper movement through the printing device, a method for determining the amount of paper passed through the printing device comprising the steps of:

a) measuring, by a microprocessor connected to the means for moving paper, a length of time the means for moving paper has moved paper through the device, said microprocessor having a volatile memory means and a timer means, said timer means timing the length of time the means for moving paper has moved paper through the device and storing a representative value of the length of time in said memory means;

b) multiplying, said representative value of the length of time the means for moving paper has moved paper through the device, stored in said memory means, by a rate that the means for moving paper moves paper through the device to produce a value representative of the length of paper moved through the device; and c) controlling the means for moving paper through the printing device in response to said value representative of the length of paper moved through the device.

39. In a printing device having a print head for inscribing paper positioned in proximity to the print head, the print head movable into and of a position to inscribe the positioned paper, a system for loading and aligning the paper in the device by moving paper along a paper path through the device comprising:

a) means for receiving the paper to be loaded into the printing device;

b) means, located along the paper path before said means for receiving the paper to be loaded, for detecting the presence of paper at said means for receiving the paper;

c) means for detecting when the print head is out of position to inscribe the paper; and, d) means, responsive to both an indication by said means for detecting the presence of paper that paper is present at said means for receiving the paper and an indication by said means for detecting when the print head is out of position that the print head is out of position to inscribe the paper, for moving paper presented at said means for receiving the paper through the printing device into a position to be inscribed by the print head when the print head is thereafter moved into a position to inscribe the paper including:

i) a cylindrical feed roller located along the paper path after said means for receiving the paper, a longitudinal axis of said feed roller located transverse to a direction of paper movement along the paper path;

ii) means for allowing said feed roller to rotate about said longitudinal axis;

iii) means for rotating said feed roller about said longitudinal axis comprising a motor having a rotating member and means for connecting said rotating member to said feed roller, said means for connecting comprising:

A) a feed roller pulley attached to one end of said feed roller, a central axis of said feed roller pulley being collinear with the longitudinal axis of said feed roller; and, B) means for transferring the rotation of said rotating member to said feed roller pulley so that rotation of said rotating member causes said feed roller pulley to rotate;

iv) means for holding the paper in contact with said feed roller comprising a snub roller having a longitudinal axis parallel to the longitudinal axis of said feed roller, the longitudinal axis of said snub roller located transverse to the direction of the paper movement along the paper path, a longitudinal length of said snub roller being relatively short compared to a longitudinal length of said feed roller, said snub roller having means for allowing said snub roller to rotate about said snub roller longitudinal axis, said snub roller contacting said feed roller, in the absence of paper, so that rotation of said feed roller causes said snub to rotate;

whereby frictional contact between said feed roller and the paper moves the paper past said feed roller and through the printing device as said feed roller rotates.

* * * * *